(12) United States Patent
Rydberg

(10) Patent No.: US 11,813,121 B2
(45) Date of Patent: Nov. 14, 2023

(54) SYSTEMS AND METHODS FOR GENERATING AN INSTRUMENT POSITIONING MAP FOR POSITIONING ONE OR MORE INSTRUMENTS ON A PATIENT BODY

(71) Applicant: OPTUM, INC., Minnetonka, MN (US)

(72) Inventor: Thomas A. Rydberg, Golden Valley, MN (US)

(73) Assignee: OPTUM, INC., Minnetonka, MN (US)

( * ) Notice: Subject to any disclaimer, the term of this patent is extended or adjusted under 35 U.S.C. 154(b) by 192 days.

(21) Appl. No.: 16/830,089

(22) Filed: Mar. 25, 2020

(65) Prior Publication Data
US 2021/0298868 A1    Sep. 30, 2021

(51) Int. Cl.
*A61B 5/287*    (2021.01)
*G06T 19/00*    (2011.01)
(Continued)

(52) U.S. Cl.
CPC .............. *A61B 90/37* (2016.02); *A61B 5/287* (2021.01); *A61B 34/10* (2016.02); *A61B 90/98* (2016.02); *G06T 7/0012* (2013.01); *G06T 19/006* (2013.01); *G16H 10/60* (2018.01); *G16H 50/20* (2018.01); *A61B 2034/104* (2016.02);
(Continued)

(58) Field of Classification Search
CPC ........ A61B 2034/104; A61B 2034/105; A61B 2090/365; A61B 34/10; A61B 5/06; A61B 5/287; A61B 90/37; A61B 90/96; A61B 90/98
See application file for complete search history.

(56) References Cited

U.S. PATENT DOCUMENTS 9,579,062 B2   2/2017   Albert
10,226,195 B2   3/2019   Briante et al.
(Continued)

FOREIGN PATENT DOCUMENTS

WO    2016/181321 A1    11/2016

OTHER PUBLICATIONS

How Is Your ECG Electrode Placement?, Oct. 30, 2015, The Student Physiologist, Online Cardiology Resource, https://thephysiologist.org/2015/10/30/how-is-your-ecg-electrode-placement/, Jun. 24, 2020.
(Continued)

*Primary Examiner* — Sin-Wai Wu
(74) *Attorney, Agent, or Firm* — Alston & Bird LLP

(57) ABSTRACT

Various methods and systems for generating an instrument positioning map for positioning one or more instruments on a patient body. The methods further correspond to tracking an image of the patient's body together with a known visual landmark positioned at a defined position on the patient's body and receiving image data, wherein the image data comprises a real-time image of the patient's body and the known visual landmark. The methods further include receiving user input identifying a mapping location of one or more instruments relative to the known visual landmark on the real-time image of the patient's body and generating an instrument positioning map for the patient by overlaying the mapping locations of the one or more instruments onto the image data, wherein the instrument positioning map comprises data locating the mapping location of each of the one or more instruments relative to the known visual landmark.

17 Claims, 26 Drawing Sheets

(51) Int. Cl.
  *G16H 10/60* (2018.01)
  *G16H 50/20* (2018.01)
  *A61B 90/00* (2016.01)
  *A61B 34/10* (2016.01)
  *A61B 90/98* (2016.01)
  *G06T 7/00* (2017.01)

(52) U.S. Cl.
  CPC ... *A61B 2034/105* (2016.02); *A61B 2090/365* (2016.02); *G06T 2200/24* (2013.01); *G06T 2207/30004* (2013.01)

(56) References Cited

U.S. PATENT DOCUMENTS

| | | | |
|---|---|---|---|
| 2016/0066805 | A1 | 3/2016 | Scherf et al. |
| 2019/0066538 | A1 | 2/2019 | Chao et al. |
| 2019/0076024 | A1 | 3/2019 | Gosink et al. |

OTHER PUBLICATIONS

Ibrahim, Mohammed, An introduction to ARKit 2—Image Tracking, Jun. 19, 2018, Medium.com, 7 pages, https://medium.com/@mohams3ios01/an-introduction-to-arkit-2-image-tracking-730fdff4e3fa, Jun. 24, 2020.

Khunti, Kirti, Accurate interpretation of the 12-lead ECG electrode placement: A systematic review, Health Education Journal, Apr. 18, 2013, Sage Journals, 6 pages, https://journals.sagepub.com/doi/abs/10.1177/0017896912472328.

Mittal, Suneet, et al., Viewpoint: Ambulatory External Electrocardiographic Monitoring: Focus on Atrial Fibrillation, Oct. 18, 2011, Elsevier, ScienceDirect, Journal of the American College of Cardiology, 24 pages, https://www.sciencedirect.com/science/article/pii/S0735109711028476, Jun. 24, 2020.

Nasco, Nasco Life/form® 15-Lead ECG Placement Trainer, Internet Archive Wayback Machine Apr. 9, 2016 to Aug. 21, 2017, Buyemp.com, 3 pages, https://www.buyemp.com/product/nasco-life-form-15-lead-ecg-placement-trainer, Jun. 24, 2020.

Reacts (unknown author), Reacts: Remote Education, Augmented Communication, Training and Supervision App, Nov. 16, 2015, YouTube, 3 pages, https://www.youtube.com/watch?v=6LqvNYJf9P8, Jun. 24, 2020.

Understanding Worid Tracking, Apple Developer Documentation, 2020 Copyright, 3 pages, https://developer.apple.com/documentation/arkit/world_tracking/understanding_world_tracking, Jun. 24, 2020.

VictoryXR, VictoryXR Victor The Torso: STEM 4d Human Anatomy Augmented Reality Learning Package | Human Torso Model (Flesh), posted on Amazon at least as early as May 10, 2019, Amazon.com, 6 pages, https://www.amazon.com/VictoryXR-Victor-Torso-Augmented-Learning/dp/B07QZTSJ34/ref=sr_1_2_sspa?th=1#detail-bullets, Jun. 24, 2020.

Vuforia, Pricing, Copyright 2020, Vuforia Engine Developer Portal, 4 pages, https://developer.vuforia.com/pricing, Jun. 24, 2020.

Walker, Andrew L. et al. "Smartphone Electrocardiogram Monitoring: Current Perspectives", Advanced Health Care Technologies, vol. 4, (2018), pp. 15-24. DOI: 10.2147/AHCT.S138445.

| PATIENT | | | | | | |
|---|---|---|---|---|---|---|
| Patient ID | Last Name | First Name | Middle Name | Date of Birth | Gender | Last Visit Date |
| 23413 | Larson | Gina | Kathryn | 08/23/2001 | Female | 02/17/2018 |
| 34722 | Smith | John | Lewis | 01/01/1960 | Male | 11/04/2019 |
| 54386 | Vander | Joseph | Reid | 06/27/1954 | Male | 07/14/2019 |

| REQUESTED ECG TEST | | | | | |
|---|---|---|---|---|---|
| Order ID | Visit ID | Request Date/Time | Status | ECG Test | ECG Device |
| 53201 | 1104 | 11/04/2019 10:23am | Pending | Holter Monitor | Welch Allyn HR 100 Holter Recorder |
| 23413 | 1072 | 05/12/2019 1:34pm | Completed | Resting/Exercise | Welch Allyn CardioPerfect |

FIG. 9

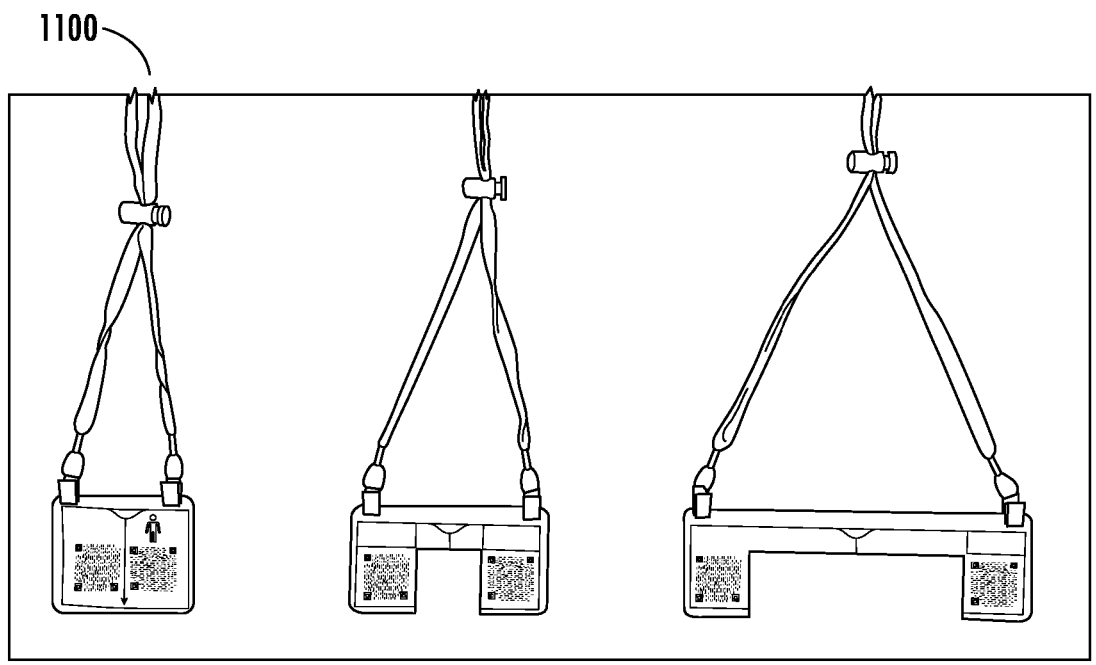
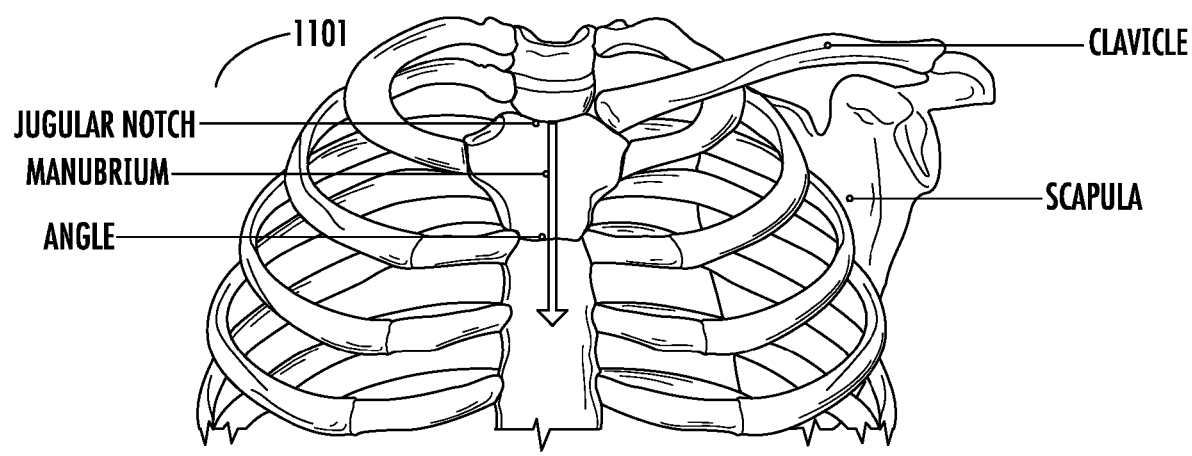
FIG. 11

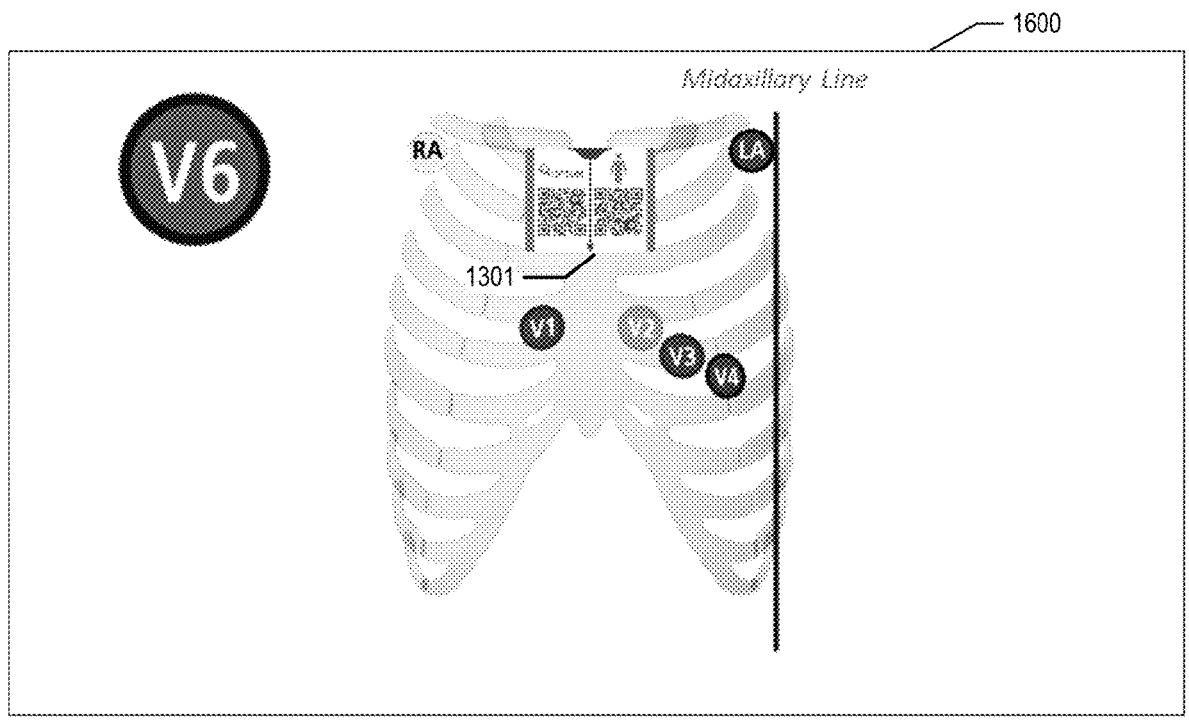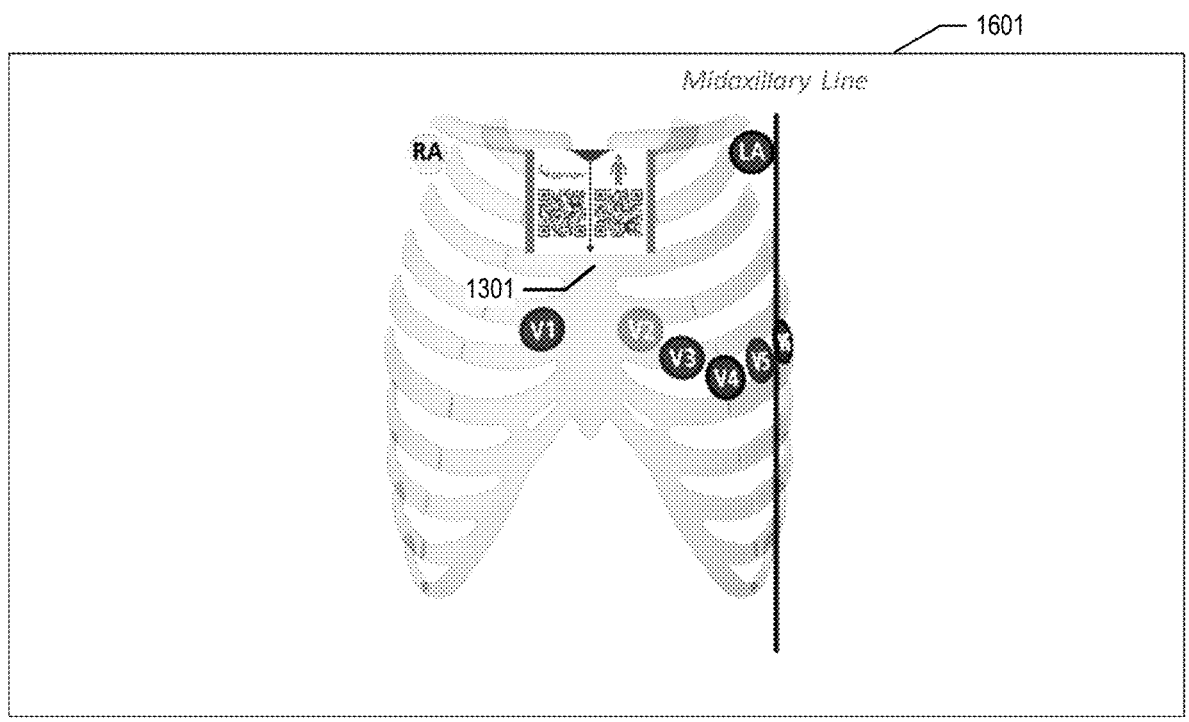
FIG. 16

SYSTEMS AND METHODS FOR GENERATING AN INSTRUMENT POSITIONING MAP FOR POSITIONING ONE OR MORE INSTRUMENTS ON A PATIENT BODY

BACKGROUND

An electrocardiogram (ECG) is commonly used in the assessment of cardiovascular disease. For example, these tools (e.g., Ambulatory ECG monitoring devices such as the Holter monitor) are configured to record electrocardiograms of a patient via a plurality of specially-placed electrodes that must be attached to the patient's torso. From these electrodes, electrical signals from the patient's body are measured and/or derived to record the average electrical activity generated and/or to monitor cardiovascular characteristics of the patient. However, these tools are carefully calibrated to the detection of signals from electrodes that must be carefully placed on defined areas of the patient's torso to properly record signals of the patient's body. These electrodes need to be positioned on the patient's torso precisely to obtain accurate signals. In certain instances, poor electrode placement can result in inaccurate signal generation, which can ultimately lead to incorrect diagnosis of the patient's healthcare issues, ineffective treatment prescriptions, and potentially increased rates of hospitalization for the patient.

When prepping a patient for ECG testing using the ECG monitor device, clinicians must remember where each electrode needs to be attached on the patient. Even a slight deviation in electrode placement of a few millimeters away from the correct position can have significant effects on the accuracy of generated signals. The placement of electrodes requires experience and training to find anatomical landmarks on patients of different shapes and sizes. Even a skilled clinician trained in using both visual and palpatory cues to identify the anatomical landmarks may still need to devote a significant amount of time for the proper placement of the electrodes. In a typical hospital setting or in an emergency, a clinician may not have the extra time to properly palpate the patient. An inexperienced clinician, a layman, or the patient may find such ECG monitor device attachment too complex. As a consequence, electrodes and ECG leads are often misplaced. Accordingly, there is a need for systems and methods for facilitating the placement of electrodes of ECG monitoring devices on patients.

BRIEF SUMMARY

In general, embodiments of the present invention provide methods, apparatus, systems, computing entities, and/or the like for generating AR-based instrument positioning maps comprising visual instrument positioning identifiers corresponding to appropriate electrode placements on a patient's body. In accordance with one aspect, a method is provided. In one embodiment, the method comprises receiving image data of a patient's body, wherein the image data comprises a real-time image of the patient's body and a known visual landmark positioned at a defined position on the patient's body; receiving user input identifying mapping locations of each of one or more instruments relative to the known visual landmark on the image data of the patient's body; generating an instrument positioning map for the patient by overlaying the mapping locations of each of the one or more instruments onto the image data, wherein the instrument positioning map comprises data locating the mapping locations of each of the one or more instruments relative to the known visual landmark; and storing the instrument positioning map for access by the patient.

In accordance with another aspect, a computer program product is provided. The computer program product may comprise at least one computer-readable storage medium having computer-readable program code portions stored therein, the computer-readable program code portions comprising executable portions configured to receive image data of a patient's body, wherein the image data comprises a real-time image of the patient's body and a known visual landmark positioned at a defined position on the patient's body; receive user input identifying mapping locations of each of one or more instruments relative to the known visual landmark on the image data of the patient's body; generate an instrument positioning map for the patient by overlaying the mapping locations of each of the one or more instruments onto the image data, wherein the instrument positioning map comprises data locating the mapping locations of each of the one or more instruments relative to the known visual landmark; and store the instrument positioning map for access by the patient.

In accordance with yet another aspect, an apparatus comprising at least one processor and at least one memory including computer program code is provided. In one embodiment, at least one memory and the computer program code may be configured to, with the processor, cause the apparatus to receive image data of a patient's body, wherein the image data comprises a real-time image of the patient's body and a known visual landmark positioned at a defined position on the patient's body; receive user input identifying mapping locations of each of one or more instruments relative to the known visual landmark on the image data of the patient's body; generate an instrument positioning map for the patient by overlaying the mapping locations of each of the one or more instruments onto the image data, wherein the instrument positioning map comprises data locating the mapping locations of each of the one or more instruments relative to the known visual landmark; and store the instrument positioning map for access by the patient.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 7A:
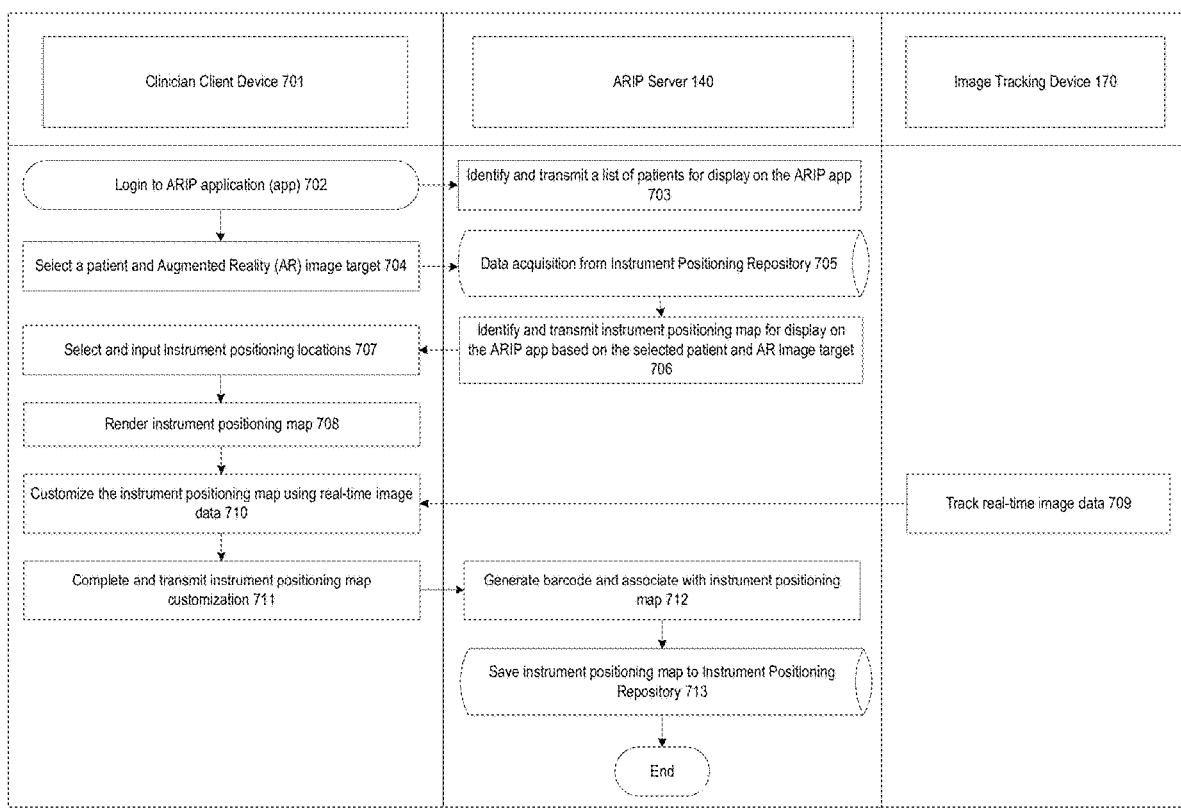
Figure 7B:
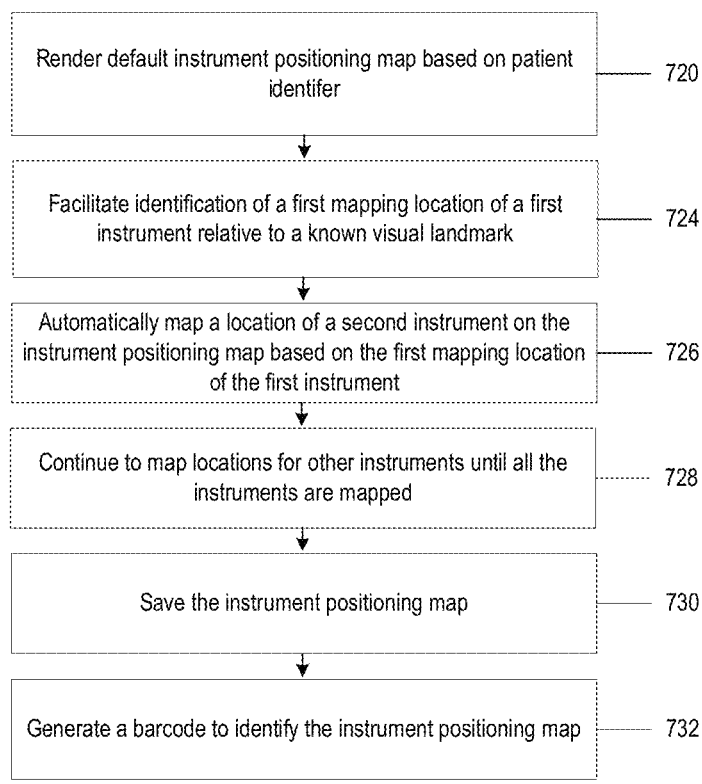
Figure 8:
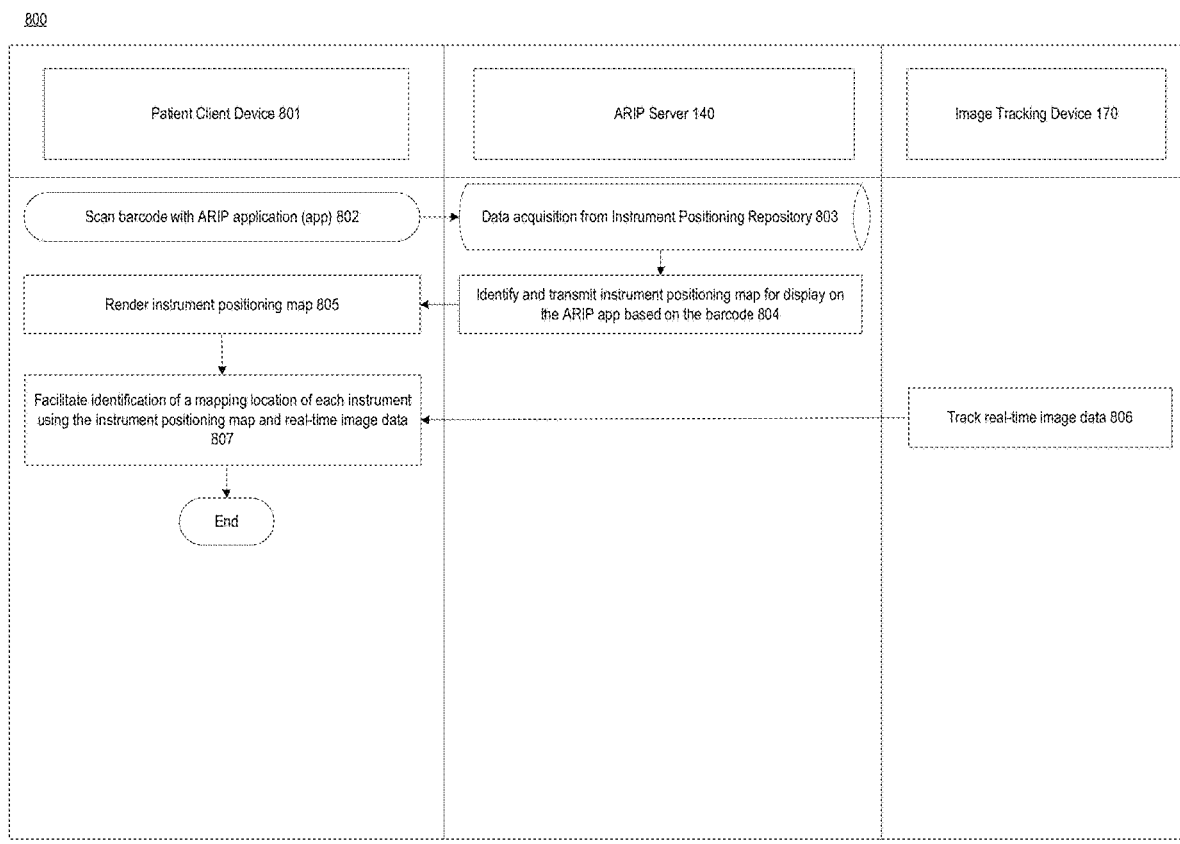
Figure 10:
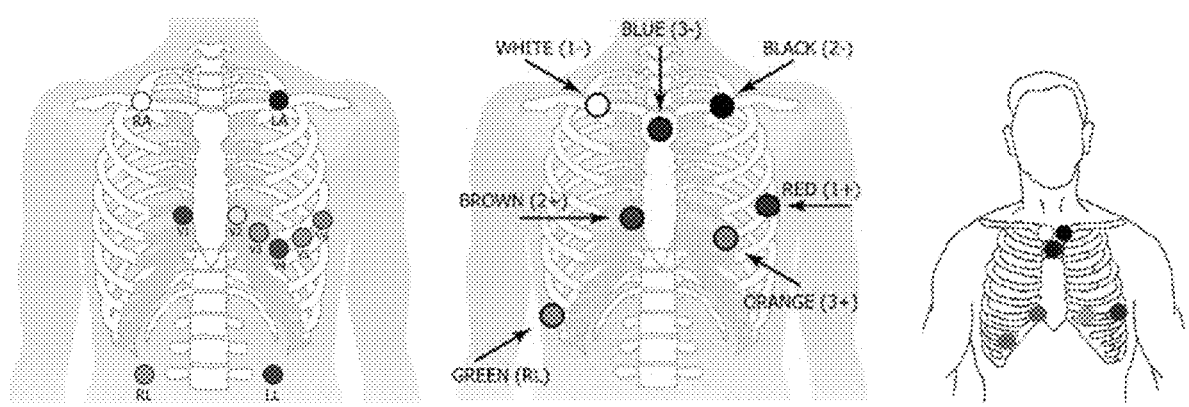
Figure 12A:
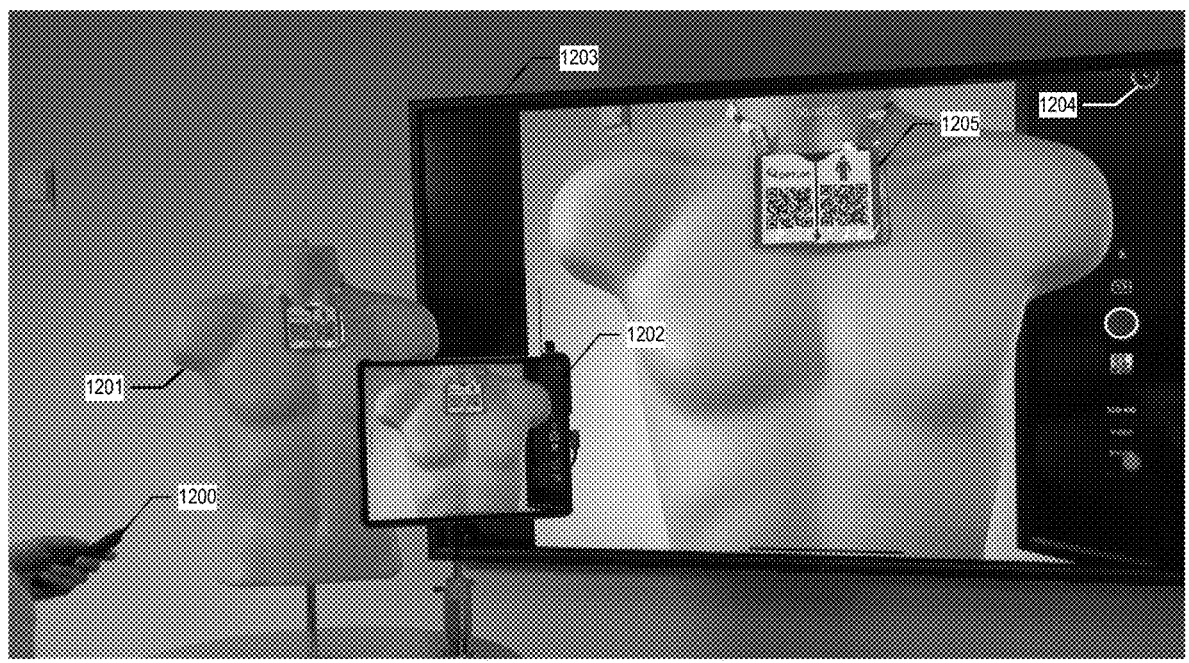
Figure 12B:
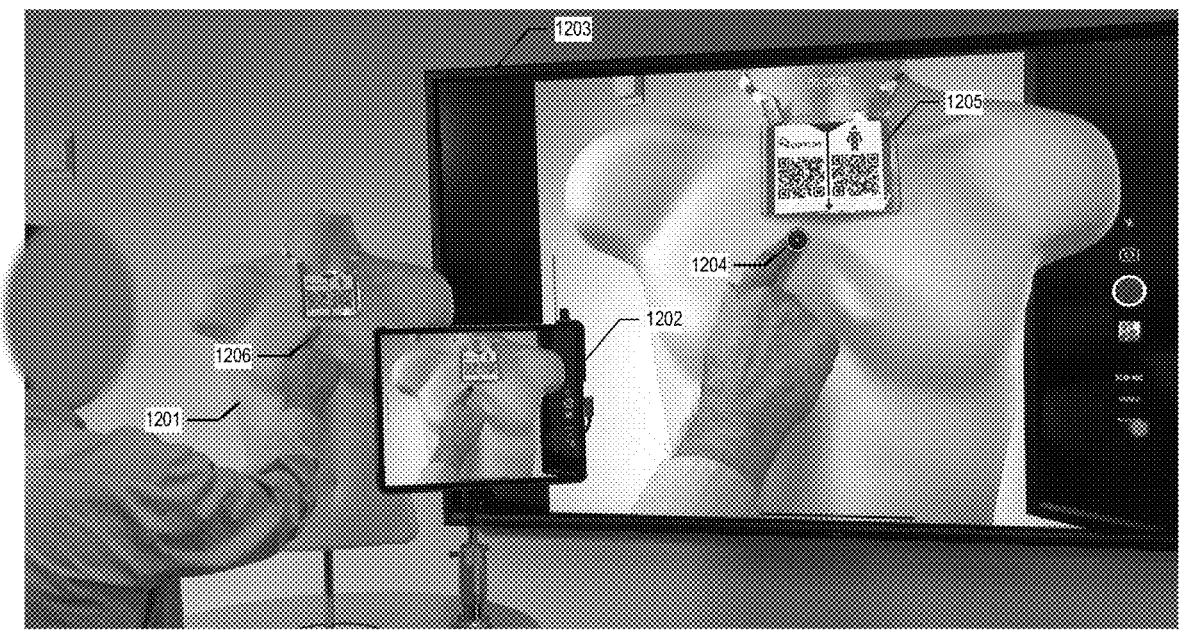
Figure 18:
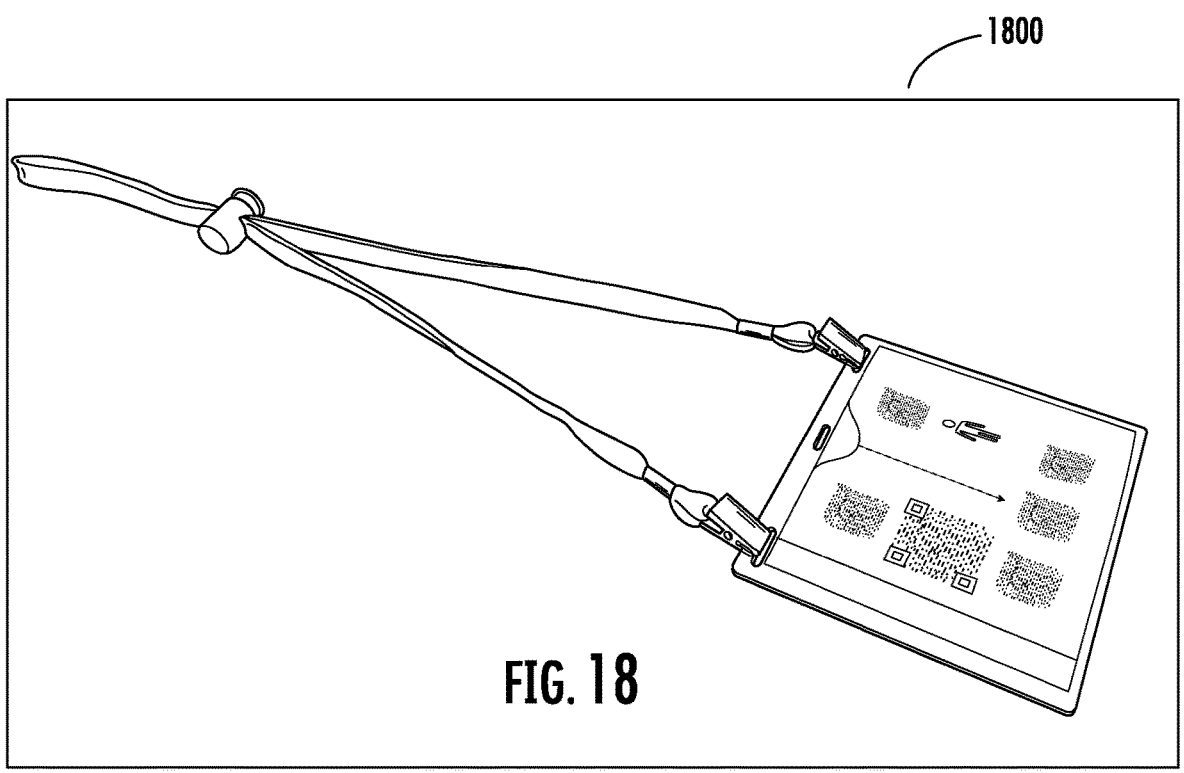

FIGS. 7A, 7B, and 8 illustrate a schematic view of data transmissions between a user computing entity and an ARIP system, according to embodiments discussed herein;

FIG. 9 illustrates an example patient data table in accordance with some embodiments discussed herein;

FIG. 10 illustrates example ECG lead configurations in accordance with some embodiments discussed herein;

FIG. 11 illustrates example ARITs and view of example anatomical landmarks in accordance with some embodiments discussed herein;

FIGS. 12A and 12B illustrate example AR-view environments in accordance with some embodiments discussed herein;

FIGS. 13-17 illustrates a step-by-step guide of proper electrode and ECG lead placements in accordance with some embodiments discussed herein; and FIG. 18 illustrates and example ARIT in accordance with some embodiments discussed herein; and FIGS. 19-24 illustrate example AR-view environments in accordance with some embodiments discussed herein;

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. OVERVIEW

Various embodiments encompass an Augmented Reality (AR) system to facilitate placement of electrodes onto a patient's body (e.g., electrodes of an ECG monitoring device). Specifically, certain embodiments are configured for generating AR-based instrument positioning maps comprising visual instrument positioning identifiers corresponding to appropriate electrode placements on a patient's body. These AR-based instrument positioning maps may be generated specifically for a particular patient, for example, through clinician-guided mapping processes, and a resulting instrument positioning map may be stored in a manner accessible to the patient via an AR-enabled device. For example, certain embodiments enable the generation of complex (e.g., 12-lead/electrode) ECG placement maps where the instrument positioning map is generated and shown to a user using graphical mapping locations in an AR view. The instrument positioning map may be used to guide a user to align an electrode with a predetermined instrument location.

Various embodiments of the invention utilize real-time image tracking of a patient's body (specifically, a patient's torso) within an AR-view environment to facilitate placement of electrodes and ECG leads by a clinician during a mapping process. Additionally, a system is provided for recording the placement of the electrodes and ECG leads via the AR-view during the mapping process, so that patients can later retrieve the generated instrument positioning map and utilize the instrument positioning map within a patient-oriented AR view to self-place the electrodes and ECG leads using the same guidance as provided by the clinician and reflected within the instrument positioning map. The guidance is provided via an AR overlay reflective of the generated instrument positioning map over the digital image of the patient's body, utilizing a known visual landmark for positioning of the instrument positioning map. The instrument positioning map of certain embodiments thus indicates where specific electrodes should be placed on the patient's body. Moreover, the AR overlay may be customized by a medical professional, for example by moving overlaid recommended electrode and ECG lead positions to better fit with the patient's body type.

A. Technical Problem

The current process for electrode and ECG lead placement is a largely error-prone, complicated, and time-consuming human-based task subject to significant potential human errors. Often, patients are given written (or visual) instructions for placement of electrodes and ECG leads, with references to anatomical landmarks (visual or otherwise) that may or may not be pronounced based on the patient's own musculoskeletal makeup. This process typically involves some guess-work on the part of the patient to translate specific locations from a skeletal system diagram to a patient's own skeleton covered by skin, muscle and adipose tissue. In a large number of cases, false ECG diagnosis resulting from improper lead placement has the potential to trigger the wasteful use of healthcare resources and even cause harm to patients.

Existing solutions to address some of these challenges such as referencing instruction manuals and diagrams provided by ECG monitoring device manufacturers, watching videos, and training with experts provide some assistance to patients, however, these solutions still do not accommodate and/or address specific musculoskeletal features of the specific patient, to minimize the likelihood of human error in placement of specific electrodes and ECG leads on a patient.

B. Technical Solution

To solve the foregoing technical problems, an exemplary embodiment of the present invention provides an AR system by utilizing AR to provide an AR visual environment and guidance of the electrodes and ECG leads' positions within the body of the patient. The AR visual environment comprises AR-based instrument positioning maps comprising visual instrument positioning identifiers corresponding to appropriate electrode placements on a patient's body. Various embodiments utilize a real-time digital image of a patient's body and a known visual landmark (e.g., image target) determined to be linked to AR content (e.g., AR-based instrument positioning maps comprising visual instrument positioning identifiers corresponding to appropriate electrode placements on a particular patient's body).

The AR system provides the AR visual environment in real time by identifying and registering a known visual landmark that is centered and vertically aligned to a patient's chest. The visual landmark is identified and compared against a reference image (e.g., known visual landmark or reference image target) of an image target database or a cloud-based image target database used for identification. If there is a match, the AR system retrieves AR content linked with the identified visual landmark and renders the AR content on a display screen of an AR device such as a head-mounted display (HMD), computer monitor, mobile device, high definition TV, and the like. After the visual landmark is identified, users (e.g., patients and clinicians) may activate a camera or the AR device to perform real-time tracking of the visual landmark positioned at a defined position on the patient's body to interact with the AR content linked to the visual landmark.

In another example embodiment, the AR system provides the AR visual environment in real time using the reference image without having to upload the reference image to the image target database or the cloud-based image target database. The reference image is stored locally on the clinician client device and/or patient client device and when the reference image is recognized in the real-world via the visual landmark, the AR system is configured to render the AR content for display.

Furthermore, this AR system coupled with the generated AR-based instrument positioning maps may serve as a training tool for clinicians and patients. The AR system includes AR training content (e.g., video of clinician-guided AR mapping processes). The present disclosure does note that according to Health Insurance Portability and Accountability Act (HIPAA) guidelines, the patient's face is never captured in accordance with certain embodiments. Any patient data and real-time images received by the AR system are temporarily displayed on the clinician client device and/or patient client device to show how the AR-based instrument positioning maps are overlaid over and positioned relative to the image of the user's body in accordance with any health organizational policies, HIPAA, or any other privacy or security laws. The AR video is provided to assist the patient in placing electrodes. This is especially beneficial for inexperienced clinicians, students, and patients in developing intuition and proper decision-making abilities with regards to the placement of electrodes. At least one advantage of generating an AR visual environment is the ability to accurately align real-time visual trackers (e.g., visual instrument positioning identifiers) on a patient's body, which are used to determine an exact position of electrodes, resulting in satisfactory feedback when positioning the electrodes with a predetermined instrument location. Accordingly, the AR visual environment can offer a rich source of information, improved documentation, and communication which will have implications for quality of service and patient health. Moreover, the AR visual environment provides step-by-step instructions to guide clinicians through selecting electrode placement according to clinician and/or ECG monitoring device manufacturer guidelines.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing entities, computing entities, and/or the like. As such, embodiments of the present invention may take the form of an apparatus, system, computing entity, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing entities, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

Figure 1:
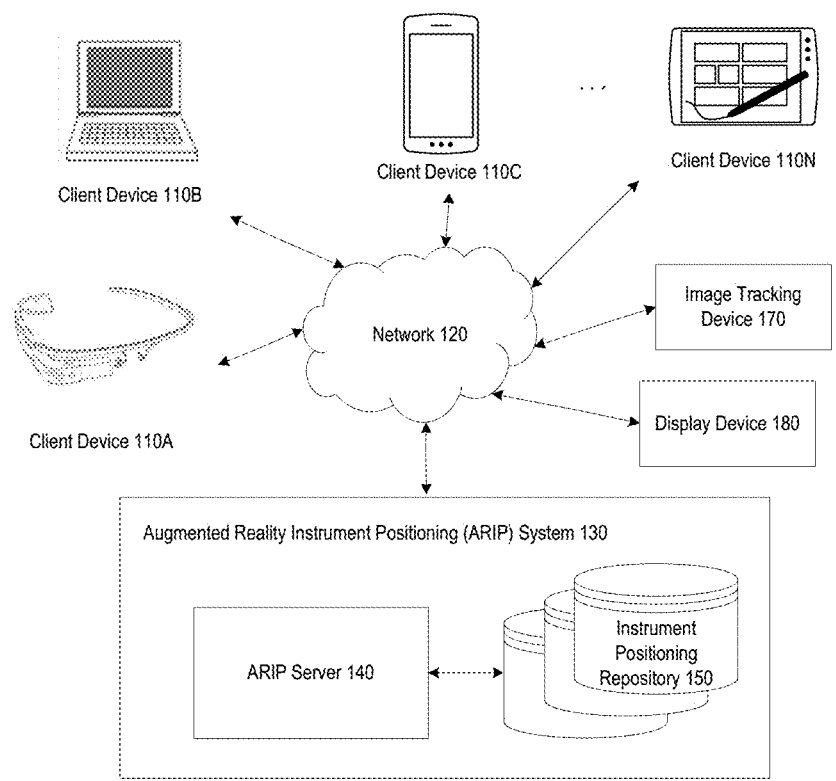
FIG. 1 is an exemplary overview of a system that can be used to practice embodiments of the present invention.

FIG. 1 provides an illustration of an exemplary embodiment of the present invention. FIG. 1 shows system 100 including an example network architecture for a system, which may include one or more devices and sub-systems that are configured to implement some embodiments discussed herein. As shown in FIG. 1, the system 100 may comprise an augmented reality instrument positioning (ARIP) system 130, one or more user computing entities 110A-110N, one or more networks 120, one or more image tracking devices 170, one or more display devices 180, and/or the like. Each of the components of the system may be in electronic communication with, for example, one another over the same or different wireless or wired networks as discussed herein.

In the example illustrated embodiment of FIG. 1, the ARIP system 130 may include ARIP server 140 and a plurality of instrument positioning repositories 150, which can be embodied as a part of, for example, circuitry 200 and/or database, among other devices (not shown). In some embodiments, the ARIP system 130 may generate complex (e.g., 12-lead/electrode) AR-based ECG placement maps (e.g., instrument positioning maps) in an AR view. The generated instrument positioning maps are stored via an instrument positioning repository 150 (shown in FIG. 1) which may be stored as a part of and/or in communication with one or more user computing entities 110A-110N and/or the ARIP system 130. The instrument positioning repository 150 may further include information accessed and stored by the one or more user computing entities 110A-110N to facilitate the operations of the ARIP system 130.

ARIP system 130 can communicate with one or more user computing entities 110A-110N, one or more image tracking devices 170, one or more display devices 180, and/or other computing entities via network 120, and a plurality of user computing entities 110A-110N may communicate with one another and/or other computing entities such as the one or more image tracking devices 170 or one or more display devices 180, via the network 120. In this regard, network 120 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, network 120 may include a cellular telephone, an 802.11, 802.16, 802.20, and/or WiMax network. Further, the network 120 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the group-based communication interface. In some embodiments, the protocol is a custom protocol of JSON objects sent via a Websocket channel. In some embodiments, the protocol is JSON over RPC, JSON over REST/HTTP, and the like.

User computing entities 110A-110N, image tracking device 170, display device 180, and/or ARIP system 130 may each be implemented as one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, wearable items/devices, items/devices, vehicles, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. The depiction in FIG. 1 of "N" user computing entities is merely for illustration purposes. Any number of users and/or user computing entities 110 may be included in the system for accessing and/or implementing aspects of the ARIP system 130 discussed herein (e.g., via one or more interfaces). In one embodiment, the user computing entities 110A-110N may be configured to display or provide AMP system interface on a display of the user computing entity for viewing, creating, editing, and/or otherwise interacting with one or more AR-based instrument positioning maps, which may be provided or pushed by the ARIP system 130 (and may be stored locally at one or more user computing entities 110A-110N). According to some embodiments, the ARIP system 130 may be configured to cause display or presentation of an interface for viewing, creating, editing, and/or otherwise interacting with one or more AR-based instrument positioning maps.

As indicated above, the user computing entities 110A-110N may be any computing entity as defined above. Electronic data received by the ARIP system 130 from the user computing entities 110A-110N may be provided in various forms and via various methods. For example, the user computing entities 110A-110N may include desktop computers, laptop computers, smartphones, netbooks, tablet computers, wearables, and the like. In embodiments where a user computing entity 110A-110N is a mobile device, such as a smart phone or tablet, the user computing entity 110A-110N may execute an "app" such as the ARIP application to interact with the ARIP system 130. Such apps are typically designed to execute on mobile devices, such as tablets or smartphones. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with location services circuitry, wired and wireless network interfaces, user contacts, and other applications. Communication with hardware and software modules executing outside of the app is typically provided via application programming interfaces (APIs) provided by the mobile device operating system.

Additionally or alternatively, the user computing entity 110A-110N may interact with the ARIP system 130 via a web browser. As yet another example, the user computing entity 110A-110N may include various hardware or firmware designed to interface with the ARIP system 130. As also shown in FIG. 1, an image tracking device (which in certain embodiments may be a part of one or more user computing entities 110A-110N) provides real-time images of a user's body (specifically, a user's torso) and additional information identifying the user or the user's environment to the ARIP system 130 (e.g., via network 120). For example, the additional information identifying the user or the user's environment may describe the physical location and orientation of the image tracking device during the image tracking, and may be provided by a GPS system, a gyroscope, and/or an accelerometer. Details on the user or a location of the user may also be provided to the ARIP system 130. The display device 180 (which in certain embodiments may be part of one or more user computing entities 110A-110N) may project AR content onto a surface or display for users to view. For example, a projector-like device that displays an AR-based instrument positioning map on the user's body (FIG. 20) or a head mounted display (HMD) with a generated AR-based instrument positioning map superimposed onto the user's body (not shown).

Figure 2:
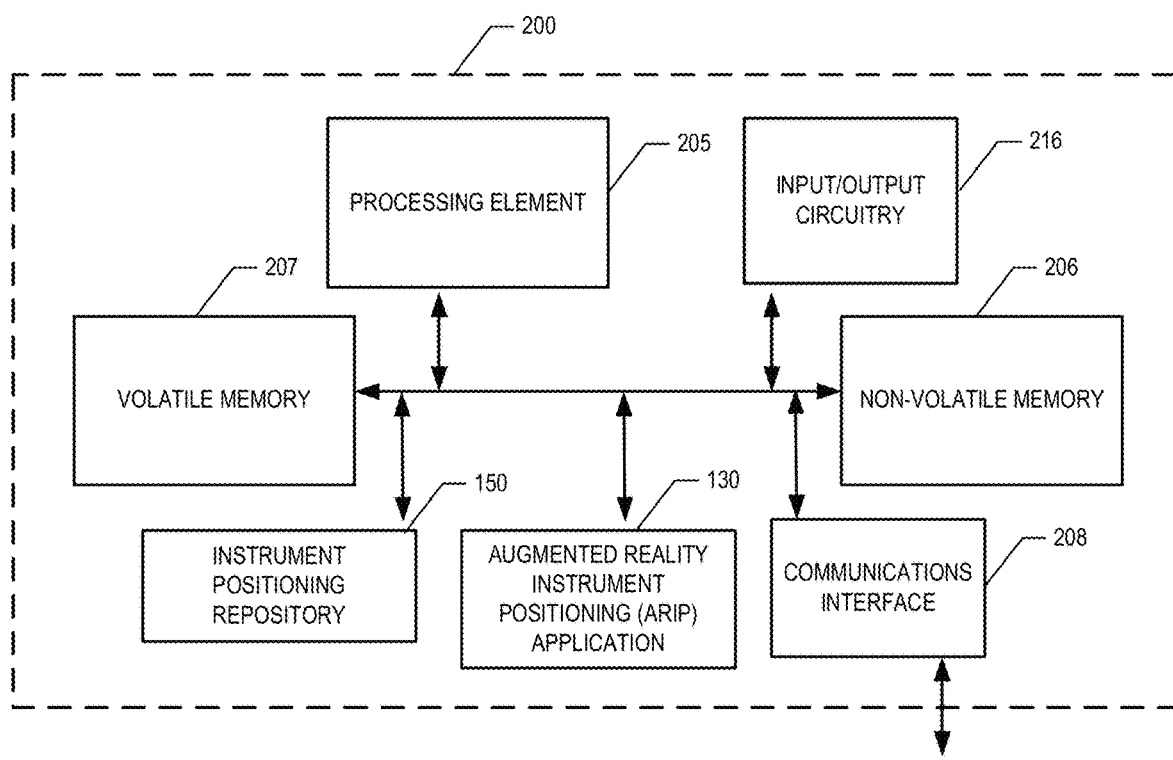
FIG. 2 illustrates an example server in accordance with some embodiments discussed herein.

A. Exemplary Circuitry of an Augmented Reality Instrument Positioning (ARIP) System FIG. 2 provides a schematic of circuitry 200, some or all of which may be included in, for example, Augmented Reality Instrument Positioning (ARIP) system 130 and/or user computing entities 110A-110N. Any of the aforementioned systems or devices may include the circuitry 200 and may be configured to, either independently or jointly with other devices in a network 120 perform the functions of the circuitry 200 described herein. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As illustrated in FIG. 2, in accordance with some example embodiments, circuitry 200 can includes various means, such as processing element 205, volatile memory 207, non-volatile memory 206, communications interface 208, instrument positioning repository 150, ARIP application 130, and/or input/output circuitry 216. As referred to herein, "circuitry" includes hardware, software and/or firmware configured to perform one or more particular functions. In this regard, the means of circuitry 200 as described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., non-volatile memory 206) that is executable by a suitably configured processing device (e.g., processing element 205), or some combination thereof.

Input/output circuitry 216 may be in communication with processing element 205 to receive an indication of a user input and/or to provide an audible, visual, mechanical, or other output to a user (e.g., provider and/or consumer). As such, input/output circuitry 216 may include support, for example, for a keyboard, a mouse, a joystick, a display, a touch screen display, a microphone, a speaker, a RFID reader, barcode reader, biometric scanner, and/or other input/output mechanisms. In embodiments wherein circuitry 200 is embodied as a server or database, aspects of input/output circuitry 216 may be reduced as compared to embodiments where circuitry 200 is implemented as an end-user machine (e.g., consumer device and/or provider device) or other type of device designed for complex user interactions. In some embodiments (like other components discussed herein), input/output circuitry 216 may even be eliminated from circuitry 200. Alternatively, such as in embodiments wherein circuitry 200 is embodied as a server or database, at least some aspects of input/output circuitry 216 may be embodied on an apparatus used by a user that is in communication with circuitry 200. Input/output circuitry 216 may be in communication with the volatile memory 207, non-volatile memory 206, communications interface 208, and/or any other component(s), such as via a bus. One or more than one input/output circuitry and/or other component can be included in circuitry 200.

Instrument positioning repository 150 and ARIP system 130 may also or instead be included and configured to perform the functionality discussed herein. In some embodiments, some or all of the functionality may be performed by processing element 205. In this regard, the example processes and algorithms discussed herein can be performed by at least one processing element 205, instrument positioning repository 150, and/or ARIP system 130. For example, non-transitory computer readable media can be configured to store firmware, one or more application programs, and/or other software, which include instructions and other computer-readable program code portions that can be executed to control each processor (e.g., processing element 205, instrument positioning repository 150, and/or ARIP system 130) of the components of circuitry 200 to implement various operations, including the examples shown above. As such, a series of computer-readable program code portions are embodied in one or more computer program goods and can be used, with a computing entity, server, and/or other programmable apparatus, to produce machine-implemented processes.

As indicated, in one embodiment, circuitry 200 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the circuitry 200 may communicate with other computing entities, one or more user computing entities 110A-110N, and/or the like.

As shown in FIG. 2, in one embodiment, the circuitry 200 may include or be in communication with one or more processing elements 205 (also referred to as processors, processing circuitry, and/or similar terms used herein interchangeably) that communicate with other elements within the circuitry 200 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the circuitry 200 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Non-volatile memory 206 may also be embodied as a data storage device or devices, as a separate database server or servers, or as a combination of data storage devices and separate database servers. Further, in some embodiments, non-volatile memory 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the relevancy prediction system may be stored. As a person of ordinary skill in the art would recognize, the information/data required for the operation of the relevancy prediction system may also be partially stored in the cloud data storage system and partially stored in a locally maintained data storage system.

Non-volatile memory 206 may include information/data accessed and stored by the ARID system 130 to facilitate the operations of the system. More specifically, non-volatile memory 206 may encompass one or more data stores configured to store information/data usable in certain embodiments.

B. Exemplary User Computing Entity

Figure 3:
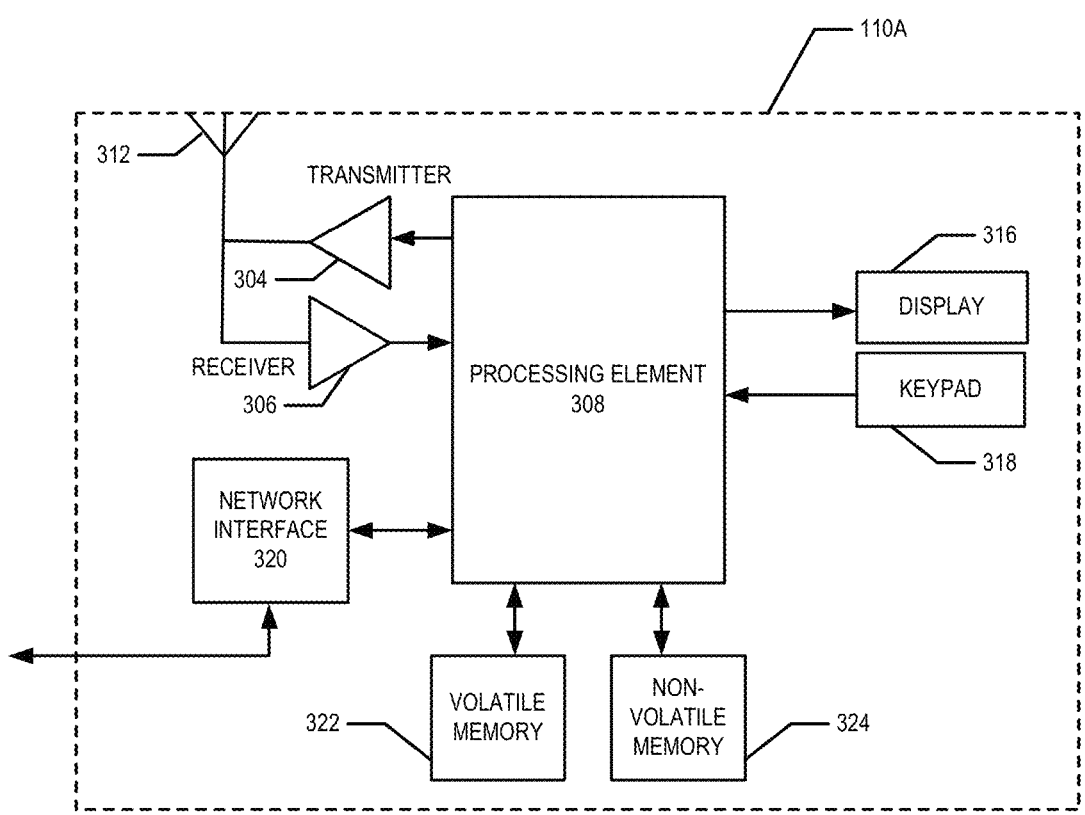
FIG. 3 illustrates an example user computing entity in accordance with some embodiments discussed herein.

FIG. 3 provides an illustrative schematic representative of user computing entity 110A-110N that can be used in conjunction with embodiments of the present invention. As shown in FIG. 3, a user computing entity 110A can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as an ARIP system 130, another user computing entity 110A, and/or the like. In this regard, the user computing entity 110A may be capable of operating with one or more air interface standards, communication protocols, modulation types, and access types. More particularly, the user computing entity 110A may operate in accordance with any of a number of wireless communication standards and protocols. In a particular embodiment, the user computing entity 110A may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 110A can communicate with various other entities using concepts such as Unstructured Supplementary Service information/data (USSD), Short Message Service (SMS), Multimedia Messaging Service (MIMS), Dual-Tone Multi-Frequency Signaling (DTMF), and/or Subscriber Identity Module Dialer (SIM dialer). The user computing entity 110A can also download changes, add-ons, and updates, for instance, to its firmware, software (e.g., including executable instructions, applications, program modules), and operating system.

According to one embodiment, the user computing entity 110A may include location determining aspects, devices, modules, functionalities, and/or similar words used herein interchangeably. For example, the user computing entity 110A may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the computing entity's position in connection with a variety of other systems, including cellular towers, Wi-Fi access points, and/or the like. Similarly, the user computing entity 110A may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE (Bluetooth Low Energy) transmitters, NFC transmitters, and/or the like. These indoor positioning aspects can be used in a variety of settings to determine the location of someone or something to within inches or centimeters.

The user computing entity 110A may also comprise a user interface device comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 110A to cause display or audible presentation of information/data and for user interaction therewith via one or more user input interfaces. As just one specific example, the user computing entity 110A may be configured to output various interface screens associated with an ARIP application, which may provide various setup/registration screens and/or may provide one or more health risk alerts for a user of the user computing entity. The user input interface can comprise any of a number of devices allowing the user computing entity 110A to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 110A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 110A can collect information/data, user interaction/input, and/or the like.

The user computing entity 110A can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 110A. Again, as a specific example, the user computing entity memory storage areas (encompassing one or both of the volatile memory 322 and/or non-volatile memory 324) may store the ARIP application thereon, which itself may encompass one or more artificial intelligence and/or machine-learning algorithms. The memory storage areas discussed herein may further encompass one or more aspects of an instrument positioning repository 150, as discussed in greater detail herein (however the sensing instrument positioning repository 150 may be stored in association with the ARIP system 130 in certain embodiments).

In one embodiment, the ARIP system 130 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the ARIP system 130 with the assistance of the processing element 205 and operating system.

As indicated, in one embodiment, the ARIP system 130 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the ARIP system 130 may communicate with computing entities or communication interfaces of other computing entities, user computing entities 110, and/or the like.

As indicated, in one embodiment, the ARIP system 130 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the ARIP system 130 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The ARIP system 130 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

User computing entity 110A may include an image tracking device such as image tracking device 170 comprising a plurality of sensors to obtain information regarding the user's body and the environment of the user computing entity 110A. Alternatively or in addition, user computing entity 110A the device can include a set of REST-based APIs so that the device can communicate with the image tracking device. The plurality of sensors of the image tracking device may include image-based sensors, such as imaging cameras or optional sensors to obtain visual information (imagery). These sensors also may include non-image-based sensors, such as Global Positioning System (GPS) receivers, accelerometers, gyroscopes, solid state compasses, radio-frequency identification (RFID), wireless interfaces (e.g., IEEE 802.11 transceivers or Bluetooth™ receivers), magnometers, ambient light sensors, and the like. In some embodiments, the ARIP system uses information from the plurality of sensors to determine one or both of a position and orientation of the image tracking device relative to the tracked imagery from the real-world environment. For example, as the user moves and interacts with real-world objects (e.g., electrodes) in the AR-view environment provided by the ARIP system 130, the image tracking device may detect changes in the position/orientation of the image tracking device (and the user's body) and render for display new AR content (e.g., the generated instrument positioning map) to overlay over the image of the user's body. Additionally, the image tracking device may detect changes in the scale, zoom, or size of the AR-view and adjust accordingly.

In some embodiments, the image tracking device 170 is configured to utilize a visual-inertial odometry technique which combines information from the plurality of motion sensors with computer vision analysis of the real-world environment visible to the tracking device 170 camera. AR processing is then performed by processing element 308 to recognize and track positions of real-world objects or features from the real-world environment.

The AR content overlaid on the digital image of the user's body is generated using AR processing by processing element 308. The AR processing performed by processing element 308 may include object identification algorithms or other AR processing techniques used to create or identify AR information or real-world objects in the digital image or video sequence. In embodiments, the ARIP system 130 may utilize the image tracking device and AR processing algorithms to identify a known visual landmark in the digital image or video sequence scene. As discussed herein, the known visual landmark may be embodied as a specially designed AR image target (e.g. comprising one or more 2D bar codes having a known orientation relative to the patient's torso) linked to an AR-based instrument positioning map. In an example embodiment, the AR image target is utilized by processing element 308 as a reference image. The reference image may be stored locally on user computing entity 110A and once detected in the real-world environment, processing element 308 triggers AR content associated with the known visual landmark to be rendered. Detecting the known visual landmark positioned at a defined position on the user's body, the ARIP system 130 may then infer the 6-dimensional space of poses (e.g., X/Y/Z positions and roll/pitch/yaw orientations) of the image tracking device with respect to the known visual marker. Thereafter, the ARIP system 130 may render the AR-based instrument positioning map and graphics or positioning identifiers that overlay the digital image of the world in such a way that the AR-based instrument positioning map and positioning identifiers would be positioned or point to specific physical locations of the user's body (e.g., right clavicle at the midclavicular line). In some embodiments, the ARIP system 130 may transmit for rendering the AR content to an AR display (e.g., smart glasses, contact lenses, a heads-up display, a digital helmet, AR headset, and the like) of the display device 180 and/or user computing entity 110A.

C. Exemplary Holter Monitor and Electrode Placement

Figure 4:
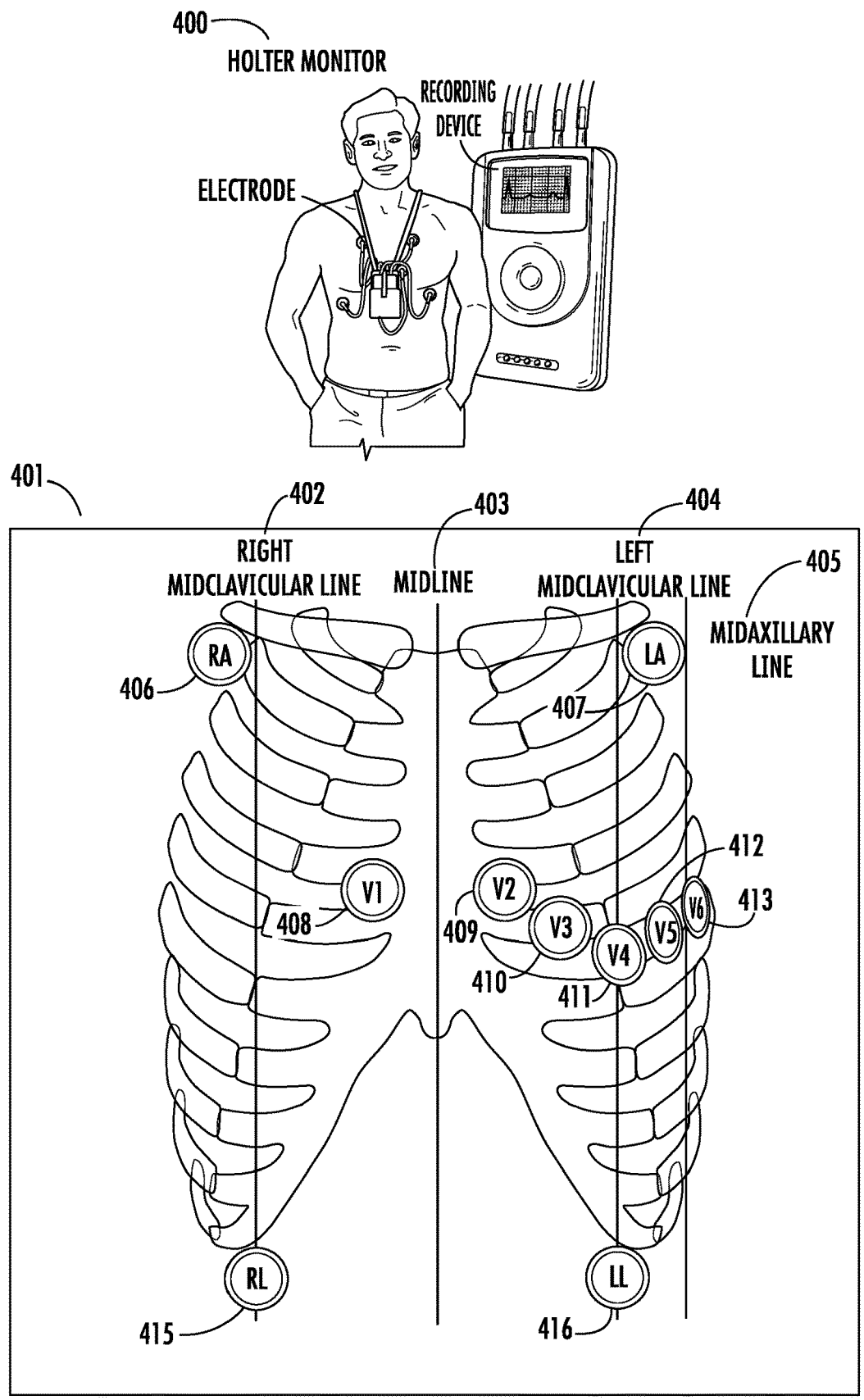
FIG. 4 illustrates an example ECG monitoring device and view of proper electrode and ECG lead placements in accordance with some embodiments discussed herein.

The ARIP system 130 includes one or more patient devices located with a patient and can be any device that gathers data from the patient such as, but not limited to, ECG, Electromyography (EMG), electroencephalogram (EEG), or Holter monitors. An example Holter monitor 400 is illustrated in FIG. 4. A Holter monitor is a small non-invasive ambulatory, portable ECG machine used to record the heart's electrical activity. This device has electrodes and electrical leads. The number and intended torso positioning of electrodes varies by model, but a 12-lead Holter monitor provides a complete picture of the heart's electrical activity by recording information through 12 different perspectives. A 12-lead Holter monitor may be preferred by some care providers for its precise ECG signal information required to analyze and detect arrhythmias and myocardial ischemia. To measure the heart's electrical activity accurately, proper electrode placement on the chest 401 is crucial. In a 12-lead ECG such as Holter monitor 400, there are 12 leads calculated using 10 electrodes. The 10 electrodes illustrated in FIG. 4 (and their corresponding intended placement) include: V1 (408)—Fourth intercostal space on the right sternum located between the right midclavicular line (402) and the midline (403); V2 (409)—Fourth intercostal space at the left sternum located between the midline (403) and the left midclavicular line (404); V3 (410)—Midway between placement of V2 (409) and V4 (411); V4 (411)—Fifth intercostal space at the left midclavicular line (404); V5 (412)—Anterior axillary line on the same horizontal level as V4 (411); V6 (413)—Midaxillary line (405) on the same horizontal level as V4 (411) and V5 (412); RA—Right Arm (406)—Anywhere between the right shoulder and right elbow; RL—Right Leg (415)—Anywhere below the right torso and above the right ankle; LA—Left Arm (407)—Anywhere between the left shoulder and the left elbow; and LL—Left Leg (416)—Anywhere below the left torso and above the left ankle. It should be understood that the illustrated positioning and electrodes are merely examples, as other monitor types may utilize different numbers and/or positioning of electrodes.

IV. EXEMPLARY SYSTEM OPERATION

The operation of various embodiments of the present invention will now be described. As discussed herein, various embodiments are directed to systems and methods for selectively and securely sharing user data with a facility to accommodate specific needs of a user.

The ARIP system 130 may be configured to provide a mobile device application such as an ARIP application (app) that is adapted to be stored in memory on the user computing entity 110A and may operate functionality related to one or more of: ECG testing preparation and patient-at-home ECG testing.

A. Exemplary Features Provided by ECG Testing Preparation

The AR ECG testing preparation module can include, for example the following features: (1) provision of an AR-view environment to facilitate placement of electrodes and ECG leads by a clinician during a mapping process using a preliminary AR-based instrument positioning map; (2) calibration of the preliminary AR-based instrument positioning map based on appropriate electrode and ECG lead placements on a patient's body and estimated electrode and lead placements utilizing a known visual landmark; (3) customization and personalization of the AR-based instrument positioning map comprising visual instrument positioning identifiers corresponding to appropriate electrode and ECG lead placements with respect to a patient's body; (4) generation and storage of a recordable AR video including the AR-based instrument positioning map so that patients can later retrieve the instrument positioning map and utilize the instrument positioning map within a patient-oriented AR view to self-place the electrodes and ECG leads using the same guidance as provided by the clinician and reflected within the instrument positioning map.

Figure 5:
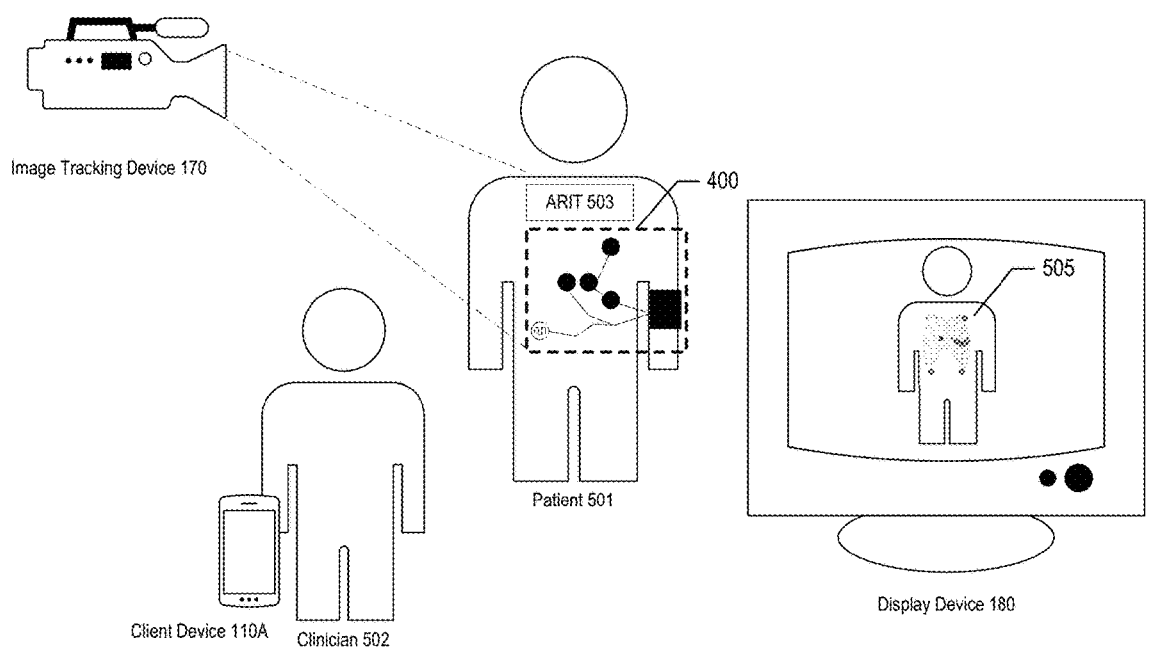
FIGS. 5 and 6 illustrates example AR-view environments in accordance with some embodiments discussed herein.

In an example embodiment illustrated by FIG. 5, the projection of the AR-view is generated by using display device 180, image tracking device 170, the AR image target (ARIT) 503, user computing entity 110A, 12-lead Holter monitor 400, or other specialized equipment. As illustrated in FIG. 5, ARIP system 130 is configured to superimpose an AR-based instrument positioning map 505 on a real-world imagery (e.g., imagery of the patient's 501 body) processed by the image tracking device 170 and display the combination of these on the display device 180 and/or the user computing entity 110A. The exact alignment of the patient's 501 body and the AR-based instrument positioning map 505 is important. As such, the ARIP system 130 is configured to accurately align both the patient's 501 body and the AR-based instrument positioning map 505 using an ARIT 503 placed at a defined position on the patient's torso, such as on the patient's jugular notch 1101 as shown in FIG. 11. The AR-view facilitates the optimal placement of electrodes of the 12-lead Holter monitor 400. This technique can be used to increase precision by providing AR-based instrument positioning maps comprising visual instrument positioning identifiers corresponding to appropriate electrode placements on a patient's body for a clinician 502 to consider and reference during the mapping process.

B. Exemplary Features Provided by Patient-Oriented-At-Home Testing

The AR ECG patient-oriented-at-home testing module can include, for example, the following features: (1) provision of an AR-view environment to facilitate placement of electrodes and ECG leads using AR-based instrument positioning maps comprising visual instrument positioning identifiers corresponding to appropriate electrode placements on the patient's body; (2) provision of feedback to the patient during placement of electrodes and ECG leads. In some embodiments the feedback is provided in real-time during the placement of electrodes and ECG leads, for example, as visual-based feedback queues, audio-based feedback queues, tactile (e.g., vibration)-based feedback queues, and/or the like, such that the feedback is useful to the patient and can provide additional guidance with regards to appropriate electrode and ECG lead placements on the patient's body.

Figure 6:
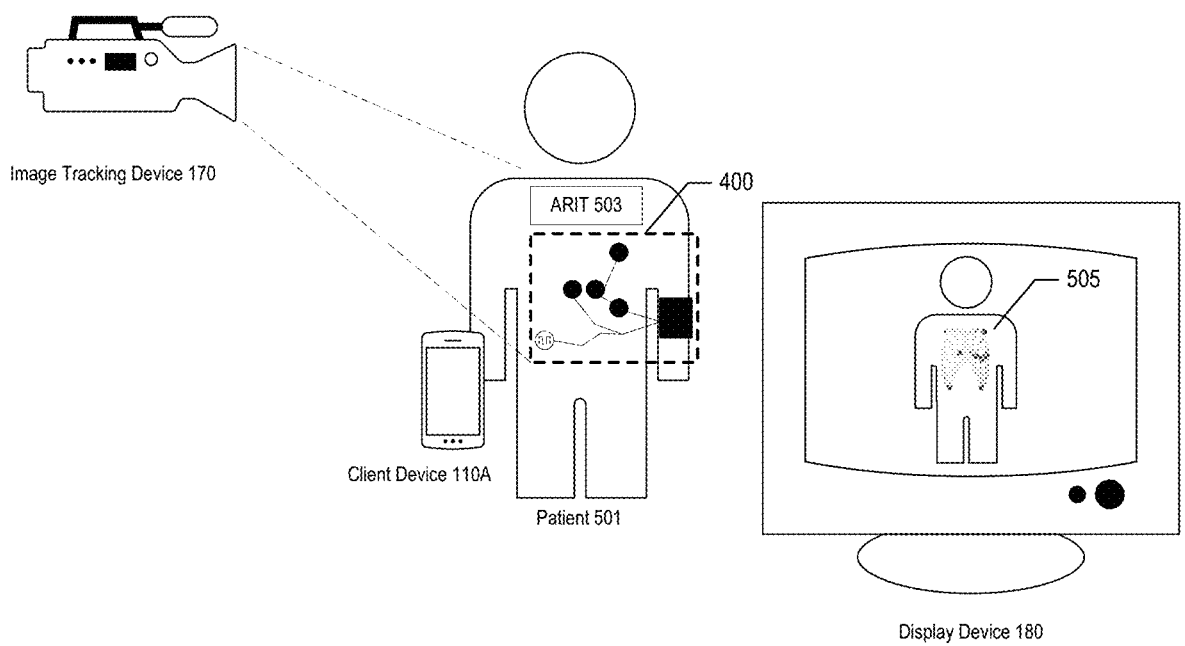

In an example embodiment illustrated by FIG. 6, patient 501 is at home and can retrieve using user computing entity 110A and ARIT 503, the generated instrument positioning map and utilize the instrument positioning map within a patient-oriented AR view to self-place the electrodes and ECG leads using the same guidance as provided by the clinician and reflected within the instrument positioning map. The patient-oriented AR-view is generated by using display device 180, image tracking device 170, the AR image target (ARIT) 503, user computing entity 110A, 12-lead Holter monitor 400, or other specialized equipment. As illustrated in FIG. 6, ARIP system 130 is configured to superimpose an AR-based instrument positioning map 505 on a real-world imagery (e.g., the patient's 501 body) processed by the image tracking device 170 and display the combination of these on the display device 180 and/or the user computing entity 110A. The exact alignment of the patient's 501 body and the AR-based instrument positioning map 505 is important. As such, the ARIP system 130 is configured to accurately align both the patient's 501 body and the AR-based instrument positioning map 505 using an ARIT 503 placed on the patient's jugular notch 1101 of FIG. 11. This patient-oriented AR-view facilitates the optimal placement of electrodes of the 12-lead Holter monitor 400. The patient 501 feels confident to position the electrodes of the Holter monitor 400 themselves with the use of the AR-based instrument positioning maps as a guide.

C. ECG Testing Prep Usage Methodology and Exemplary Data Flow

FIGS. 7A and 7B illustrate various interactions between the following system components show in FIG. 1: clinician user computing entity 701, ARIP server 140, and image tracking device 170. Referring now to FIG. 7A, the process illustrates example operations performed by ARIP server 140 for generating the instrument positioning map for a particular patient and associating the instrument positioning map to a visual landmark (e.g., ARIT).

The process illustrated in FIG. 7A starts at step 702 where the clinician user computing entity 701 logs in to the ARIP application (app). In this case, the ARIP server 140 provides the ARIP app and upon activation of the ARIP app by the clinician user computing entity 701, provides a login interface that facilitates entering a valid username and password. The ARIP server 140 authenticates the entered username and password, and then redirects the ARIP app to an appropriate graphical user interface if the authentication is successful. In step 703, the ARIP server 140 identifies and transmits a list of patients for display on the ARIP app. When logged in as a clinician account, the clinician accesses an ECG testing preparation interactive support interface comprising the list of patients. Alternatively, if the patient logs in, the patient accesses the patient-at-home ECG testing interactive support interface which is discussed in further detail below. In other embodiments, the clinician-specific and patient-specific functionality may be separated into different apps (a clinician-specific app and a patient-specific app). In such embodiments, a patient attempting to log into the clinician specific app may receive an error message with instructions redirecting the patient to install the patient-specific app. Similarly, a clinician attempting to log into the patient-specific app may receive an error message with instructions redirecting the clinician to install the clinician-specific app.

In step 704, the clinician user computing entity 701 displaying the ECG testing preparation support interface further provides the clinician the ability select a patient and an AR image target. As shown in FIG. 10 a number of precordial (e.g., chest) electrodes and placements are required. The clinician must be careful to select to an AR image target that does not cover any of the electrode mapping locations shown in FIG. 10. In some embodiments, the ARIP server provides a recommended image target based on the Holter/ECG monitor associated with the patient. To facilitate selection of a patient, the ARIP server displays a listing of patients as shown in an exemplary list of patients illustrated by tables 900 and 903 of FIG. 9. Table 900 illustrates a list of registered patients where each patient row 902 includes patient information 901 including the patient identification, last name, first name, middle name, date of birth, gender, and last visit date (e.g., last visit with the clinician). Once the clinician using the clinician user computing entity 701 selects a particular patient such as, for example patient John Smith, the ECG testing preparation support interface renders for display table 903 illustrating a list of requested ECG tests. Each row 905 of table 903 includes ECG test information 904 including the ECG order identification, the visitation identification, the requested date and time for the ECG test, the status of the ECG test, the ECG test, and the ECG device.

Returning to FIG. 7A, upon the clinician selecting a particular patient and associated ECG test, the ARIP server 140 is configured to acquire data from the instrument positioning repository as shown in step 705. The data retrieved from the instrument positioning repository is data related to the selected patient. In step 706, the ARIP server 140 is configured to identify and transmit an instrument positioning map for display on the ARIP app based on the selected patient and AR image target. Thereafter, as shown in step 707, the clinician user computing entity 701 displaying the ECG testing preparation support interface further provides the clinician the ability select and input instrument positioning locations (e.g., electrode position markers). The clinician's selection and input of the instrument positioning locations is based at least in part on the identification of the physiological characteristics and anatomical landmarks of each patient. In an example embodiment, the ARIP server 140 may be configured to cause to display on the ARIP app electrode placement guidelines provided by ECG monitoring device manufacturers. In this case, the clinician may thoughtfully input the instrument positioning locations using the ARIP app electrode placement guidelines provided by ECG monitoring device manufacturers. Consistent with health organizational policies, HIPAA, or any other privacy or security laws, such ARIP app electrode placement guidelines or any training content, media, or video provided by the ARIP app will utilize generic references and images, such as three-dimensional (3D) computer generated imagery (CGI) models of a human body. Additionally and in some embodiments, the clinician user computing entity 701 displaying the ECG testing preparation support interface further provides the clinician the ability to reposition each instrument positioning location. In an example embodiment, the ARIP server 140 may be configured to update one or more instrument positioning locations based on the clinician repositioning an instrument positioning location.

Figure 19:

In step 708, the instrument positioning map 707 is rendered to the clinician user computing entity 701. FIG. 19 illustrates an exemplary instrument positioning map projected on a display device 1900 using AR image target 1901 (e.g., ARIT). In step 709, the image tracking device 170 is configured to track real-time data comprising the patient's torso as illustrated in FIGS. 5 and 6. In step 710, the clinician using the clinician user computing entity 701 may customize the instrument positioning map using the real-time image data. Upon completion of the customization of the instrument positioning map as depicted, the clinician user computing entity 701 transmits the customized instrument positioning map to the ARIP server 140 using the ARIP app as depicted in step 711. In response, the ARIP server 140 generates a barcode (e.g., a two-dimensional barcode or other unique identifier) and associates the barcode with the instrument positioning map as depicted in step 712. In step 713, the ARIP server 140 is further configured to save the instrument positioning map to the instrument positioning repository for later retrieval.

FIG. 7B illustrates the clinician-guided mapping process utilizing a real-time image tracking of patient's body (specifically, a patient's torso) within an AR-view environment to facilitate placement of electrodes and ECG leads. In step 720 the ARIP server 140 is configured to render a default or preliminary AR-based instrument positioning map based on a patient identifier. The patient identifier may be any patient identifying data such as the patient's chest size or testing needs in order to select the appropriate ECG monitor. To properly render the instrument positioning map onto the patient's body, an ARIT is utilized and placed on the surface of the patient's body at a known location and thus provides the ARIP server 140 with points of reference. In the specific embodiment of the figures, the clinician places a neck lanyard including the ARIT on the patient so a marker (e.g., the black shape at the top of the ARIT) as shown by drawing 1100 of FIG. 11 overlays the patient's jugular notch 1101. In some embodiments, the neck lanyard includes a barrel cord lock (or other adjustment feature) which can be adjusted to hold the image target in position. As can be seen in drawing 1100, AR image targets (ARIT) may be provided and/or generated in different sizes, shapes, and with different barcodes for each patient. Such variations in sizes and shapes may be provided to accommodate differences in patient sizes, posture, or electrode placements.

After placement of the ARIT on the torso as shown in FIG. 12A, the clinician may initiate the mapping process using an "app" such as the ARIP application. Similar to FIG. 5, FIG. 12A includes a display device 1203 and/or user computing entity 110A, image tracking device 1202, the ARIT 1205, or other specialized equipment such as a wireless air mouse 1200 or other non-contact control responsive to gestures or movements of the user. As illustrated in FIG. 12A, the ARIP application displays on the display device 1203 a digital image comprising the patient's torso or in this example, a mannikin 1201. The ARIP application is further configured to superimpose a mapping location marker 1204 (e.g., visual marker cue), using the wireless air mouse 1200, on the displayed real-world imagery of the mannikin 1201 processed by the image tracking device 1202.

In some embodiments, movement of wireless air mouse 1200 may be translated by the ARIP application into movement of the mapping location marker 1204 on the display screen of the display device 1203. Referring now to 12B, to begin the present invention's execution of the AR-based instrument positioning map guidance, the clinician places his finger 1206 over a first electrode position on the mannikin 1201 and then uses the wireless air mouse 1200 or some other mechanism for electronically recognizing the location of the clinician's finger to mark the location in the AR environment, thereby setting the desired location of the first electrode. Thus, in the present example, the mapping location marker 1204 assists the clinician in identifying the location at which the clinician must correctly position the first electrode, as shown in the included visualization on the display device 1203 in FIG. 12B.

In some embodiments, using the clinician's finger and the wireless air mouse 1200 (or other mechanism for electronically recognizing the location of the clinician's finger), the clinician is able to select specific instrument positioning locations of the patient's torso. In other words, the clinician identifies the patient's anatomical landmarks and inputs or applies, using wireless air mouse 1200, instrument positioning location markers, such as circle shapes, square shapes, etc. Other types of markers can be inserted as AR content, such as comments, audio, or links. Once the instrument positioning location markers are inputted by the clinician and tracked or detected by the ARIP application, they are recorded and displayed. The ARIP application is then configured to associate the one or more instrument positioning location parameters (e.g. x, y, and z locations in 3D space) and recordings to the ARIT 1205 and is stored locally on the clinician client device and/or the physician client device. In this case the instrument positioning locations and the ARIT 1205 are linked.

FIGS. 12A and 12B illustrates an example proper placement of the ARIT at a known location so as to enable the ARIT to be used as a known visual landmark on the patient's torso in order to facilitate identification of a first mapping location of a first instrument relative to a known visual landmark (e.g., ARIT) as depicted in step 724. As shown in FIGS. 12A and 12B, a clinician may begin by placement of a first electrode within the AR environment, however it should be understood that in certain embodiments, additional setup may be required. For example, with reference briefly to FIG. 13, the clinician may first locate the left and right clavicular lines extending parallel with the length of the patient's torso (e.g., vertically, while the patient is standing) in a manner similar to that discussed in reference to FIGS. 12A and 12B. The left and right clavicular lines (or other reference lines/points placed onto the patient's torso within the AR environment) may be used as reference points for later placement of electrodes, such as in accordance with the processes and methods as discussed herein.

Figure 13:
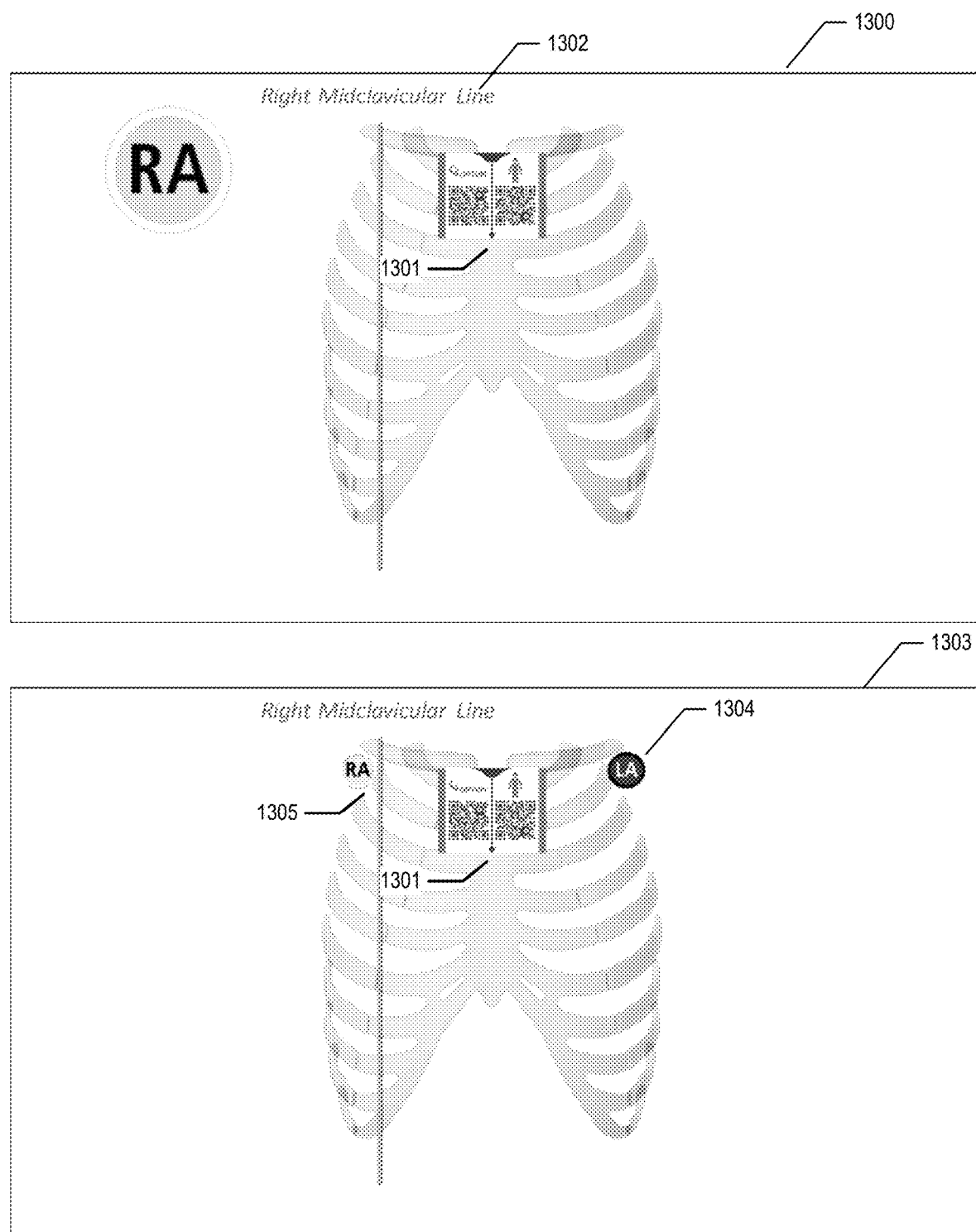
Figure 14:
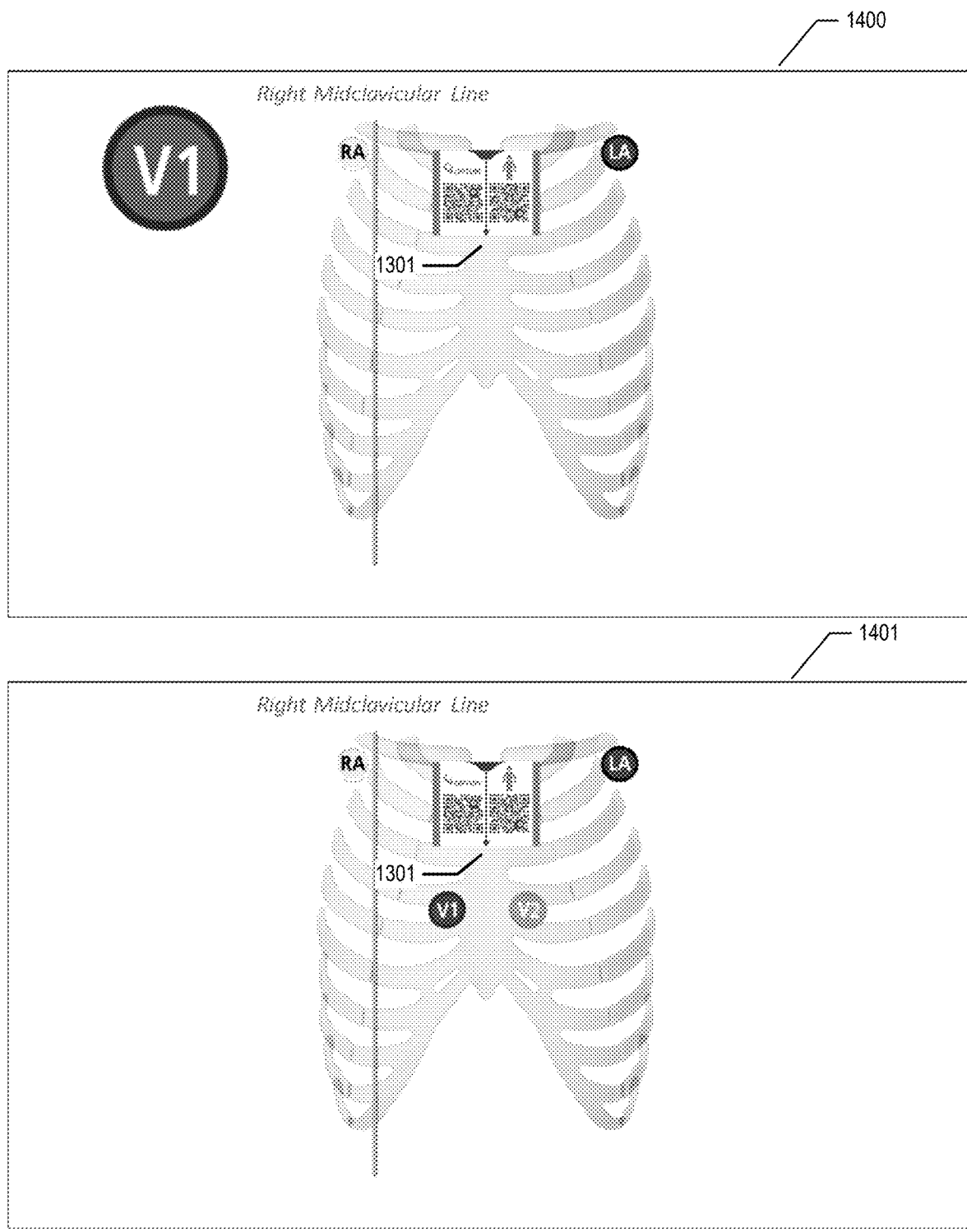
Figure 15:
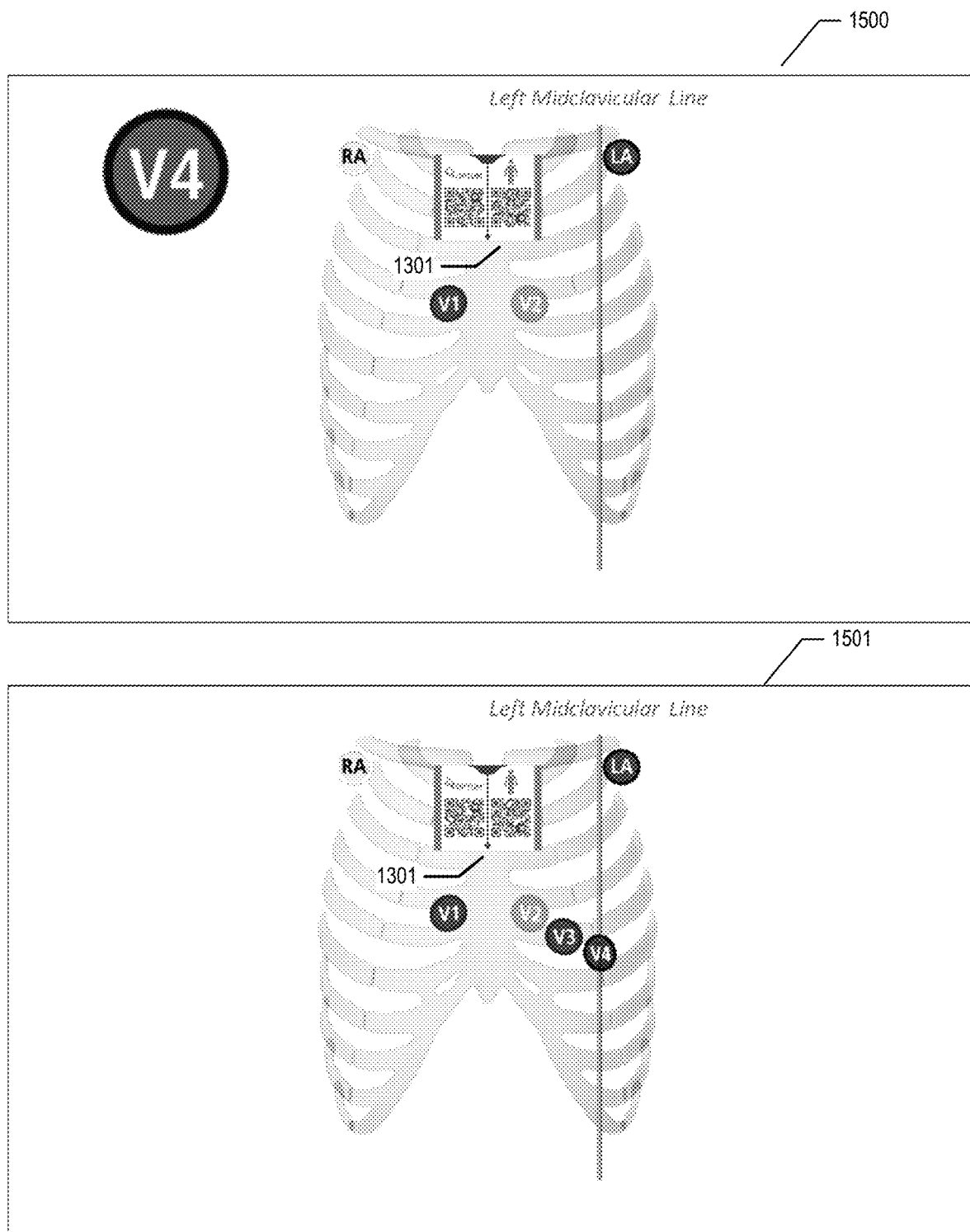
Figure 17:
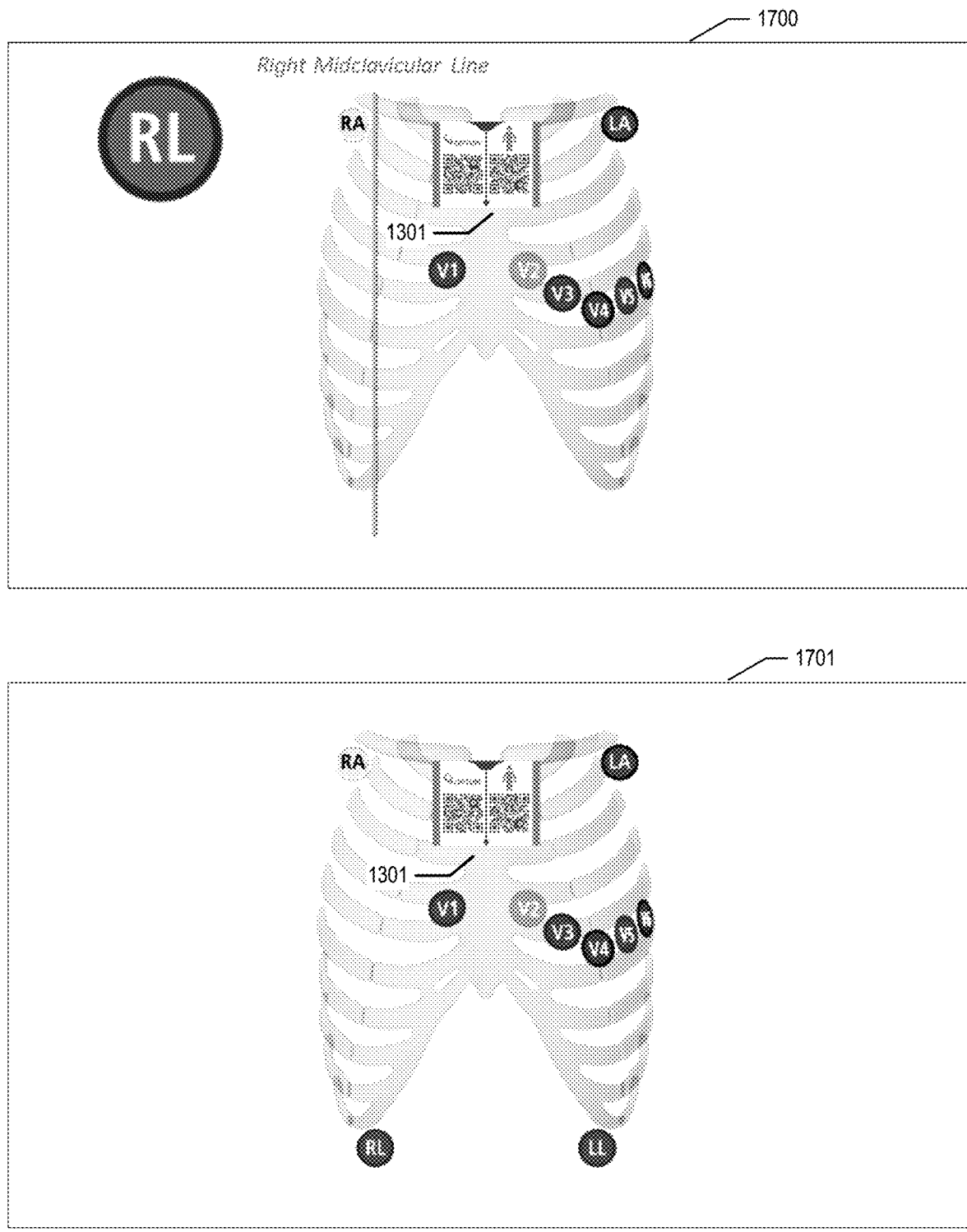

In step 726, the ARIP server 140 is configured to automatically map a location of a second instrument on the instrument positioning map based on the first mapping location of the first instrument. Once the clinician or patient places the ARIT on the patient, invokes the ARIP app on their user computing entity, and scans the ARIT to render the AR-view, guidance is provided via an AR overlay reflective of the generated instrument positioning map over the digital image of the patient's body. For example, FIG. 13 illustrates the AR overlay positioned using the ARIT 1301 providing guidance to the clinician to locate the Right Arm (RA) 1305 electrode location below the patient's right clavicle, and between the right midclavicular line 1302 and shoulder. Once the first mapping location (e.g., RA 1305) is identified by the clinician marking the location of the first instrument using a wireless air mouse, a second instrument location (e.g., electrode location) may automatically be identified, for example, if the second instrument location is dependent on the positioning of the first mapping location. For example, the Left Arm (LA) 1304 electrode mapping location is automatically added and displayed in a mirror position to the RA 1305 mapping location.

Returning to FIG. 7B and step 728, the ARIP server 140 is configured to continue mapping locations for other instruments (e.g., electrodes) until all the instruments are mapped. Guidance for selecting the remaining electrode positions V1-V6, Left Leg (LL), and Right Leg (RL) is illustrated in FIGS. 13-17 using the AR overlay reflective of the generated instrument positioning map over the digital image of the patient's body. The remaining electrode positions may be set by a clinician in a manner as discussed above in reference to the first and second electrode positions, for example, with the clinician selecting a specific location on the patient's torso and electronically marking the location, thereby placing an electronic marker on the imagery of patient's torso within the AR environment corresponding to a particular electrode. The electrodes may be placed in series, such that a clinician sequentially marks the location of each of the plurality of electrodes, and the ARIP server 140 sequentially stores the locations of these electrodes as discussed herein. In step 730, the ARIP server 140 is configured to save the instrument positioning map and thereafter as depicted in step 732, the ARIP server 140 is configured to generate a barcode (or other unique identifier) to identify the instrument positioning map. This barcode contains (or links to a data storage repository containing) the instrument positioning map comprising the electrode position data for this patient, thereby capturing the clinical guidance that will benefit the patient at home.

D. Patient-At-Home Testing Application Usage Methodology and Exemplary Data Flow FIG. 8 illustrates various interactions between the following system components show in FIG. 1: patient user computing entity 801, ARIP server 140, and image tracking device 170. Process 800 illustrates example operations performed by ARIP server 140 for provisioning the instrument positioning map for a particular patient at home. At this point in ECG testing, the patient has undergone the clinician-guided mapping processes and is equipped with the ARIT used to render the instrument positioning map and the Holter monitor. An example ARIT 1800 used by the patient is illustrated in FIG. 8.

Process 800 begins with step 802 where the patient user computing entity scans the barcode found on the ARIT with the ARIP app or otherwise provides data indicative of a unique identifier associated with the patient-specific electrode mapping. In step 803, the ARIP server is configured to retrieve the instrument positioning map associated with the barcode (or other unique identifier) from the instrument positioning repository and any supplementary data (e.g., instructional video providing information regarding how to wear the neck lanyard and ARIT, an electronic pdf guide of the mapping locations of the various electrodes, other educational information, etc.). In step 804, the ARIP server identifies and transmits the instrument positioning map for display on the ARIP app based on the barcode. In step 805, the instrument positioning map is rendered on the patient user computing entity 801. In step 806, the image tracking device 170 is configured to track real-time image data and in step 807, the patient user computing entity 801 is configured to facilitate identification of a mapping location of each instrument using the instrument positioning map and the real-time image data.

In an example embodiment, the ARIT may be placed in a field of view of the image tracking device 170 at a predetermined position on the patient's body as determined during the clinician-guided mapping process. The ARIT serves as a reference point. The instrument positioning map may be overlaid in relation to a position, orientation, and size of the ARIT in the real-world environment. In this case, the ARIP server will overlay the instrument positioning map on the real-time image data and will further align the instrument positioning map to the orientation and scale of the real-time image scene (e.g., patient's body) even if the patient moves around.

The ARIT is analyzed by the ARIP server to determine the instrument positioning map. As discussed above, each ARIT includes an instrument positioning map unique to a particular patient. The ARIP server may then provide on the display of the patient user computing entity 801, an AR-view comprising a real-time view seen through the image tracking device 170 overlaid with the instrument positioning map. The instrument positioning map is displayed according to the size, position, and orientation of the ARIT.

Upon rendering for display the AR overlay reflective of the generated instrument positioning map over the digital image of the patient's body, utilizing the ARIT of the instrument positioning map, the relative location of the one or more instruments (e.g., electrodes and ECG leads) may be determined. In an example embodiment, one or more mapping locations of each instrument is displayed on the instrument positioning map for positioning and orienting on the patient's body of the real environment for AR visualization. In some embodiments, the mapping locations may all be displayed simultaneously, or the mapping locations may be displayed sequentially, so as to guide the patient in a step-by-step fashion regarding how to place the instruments. For example, the ARIP app may provide an option to view a step-by-step guide and the ARIP app is configured to display a breakdown of the individual step-by-step instrument mapping locations. In some embodiments the step-by-step guide option may allow the user to move sequentially through the step-by-step guide. Additionally or alternatively, the ARIP app may provide an option to view a completed guide in which the ARIP app is configured to simultaneously display all the instrument mapping locations on the instrument positioning map. In other words, the entire collection of instrument mapping locations are simultaneously displayed and may be arranged so that all of the instrument mapping locations appear separately from each other.

Figure 20:

FIG. 19 illustrates one example display that may be provided to a patient to facilitate placement of a plurality of electrodes on a patient body. As illustrated in FIG. 19, the patient is prompted by the ARIP app with an instructional video to align the top of image target 1901 with his/her jugular notch, or other anatomical landmark if applicable, such that the image target may be used as a visual landmark used for reference against the placement of the electrodes. The ARIP is then configured to display a patient-oriented AR view 1900 to self-place the electrodes and ECG leads using the same guidance as provided by the clinician and reflected within the instrument positioning map. As can be seen in FIG. 20, the instrument positioning map moves and may be repositioned according to the patient's detected body movement.

E. AR-Based Instrument Positioning Map

Figure 21:
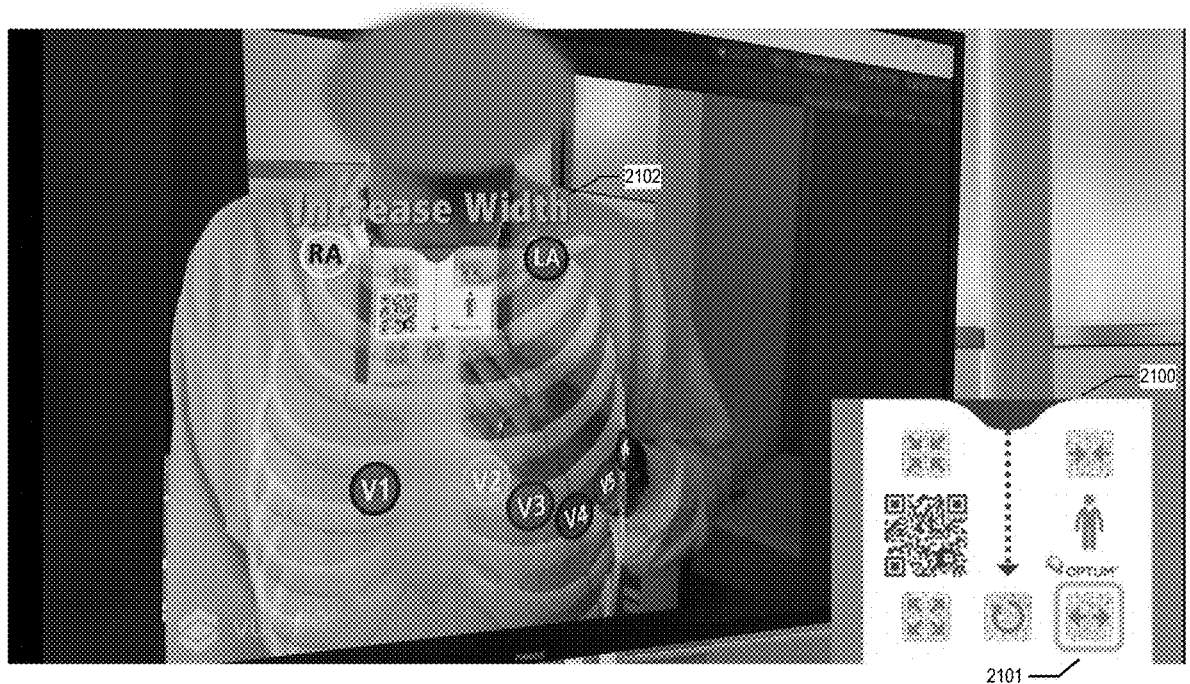

In an example embodiment, the ARIP app is further configured to manipulate the AR-view as depicted in FIGS. 21-24. FIG. 21 illustrates operations related to AR-view enhance actions for manipulating the instrument positioning map. In an example embodiment the user may move, turn, walk around as long as the ARIT can be tracked and processed by the ARIP app. In an embodiment, when a change in movement is detected by the ARIP app, the instrument positioning map is provided in a geometrically correct orientation with respect to change of movement by the user. The instrument positioning map may be determined to be properly positioned when the ARIT is just below the user's right clavicle. If the ARIT is not properly positioned, a warning that the ARIT is not properly positioned may be displayed to the user via the ARIP app. In another example embodiment, if the ARIT is obstructed in any way, the ARIP app may not render the instrument positioning map and may further provide a warning to the user.

Once the ARIT is properly positioned, the instrument positioning map is generated and shown to the user using graphical mapping locations in an AR view. The ARIT may be determined to be properly positioned when image target requirements for the instrument positioning map are satisfied. For example, the image target requirements may correspond to image quality factors (e.g., distance ARIT is from the image tracking device, etc.) that should be satisfied before the instrument positioning map is generated.

Figure 22:
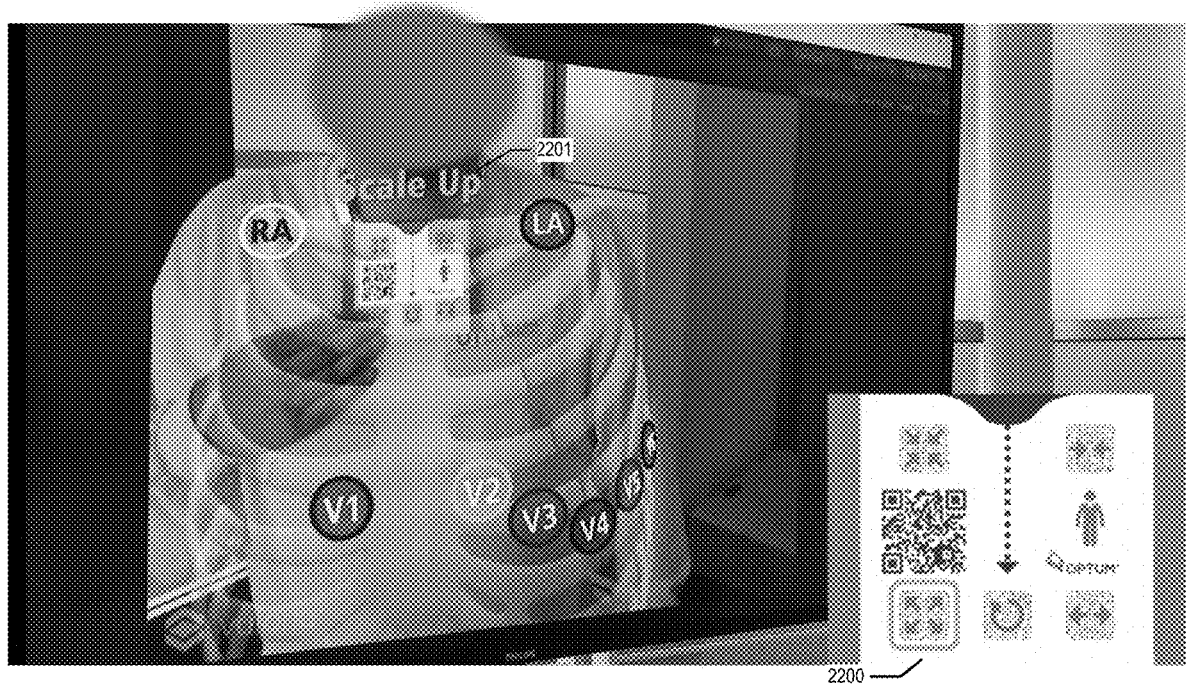
Figure 23:
Figure 24:
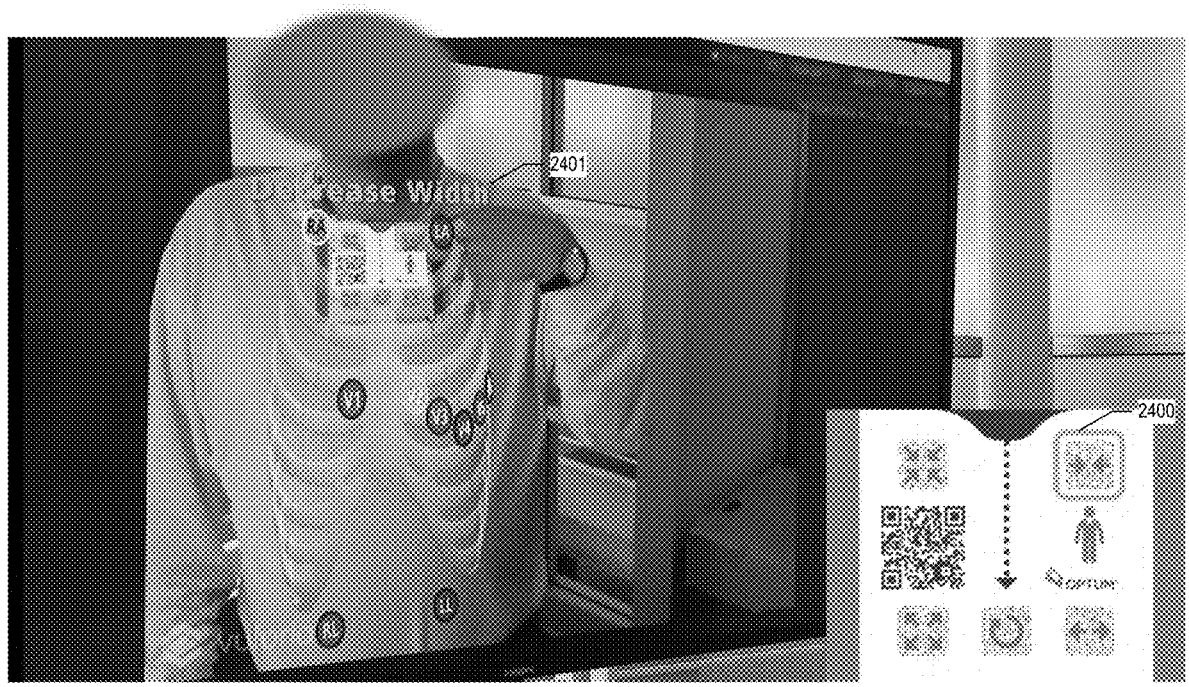

In some embodiments, the user may be allowed to change the appearance of the instrument positioning map. As shown in FIG. 21, the ARIP app provides a resizing graphical user interface 2100 comprising a variety of actions to re-size the AR overlay reflective of the generated instrument positioning map over the digital image of the patient's body. For example, upon selecting action 2101, the instrument positioning map increases its width up to a predetermined limit. In FIG. 22, the ARIP app provides an action 2200 to scale up 2201 the instrument positioning map to a predetermined limit. In some embodiments, the ARIP app is further configured to scale up the mapping locations. In FIG. 23, the ARIP app provides an action 2300 to scale down 2301 the instrument positioning map to a predetermined limit. FIG. 24 illustrates the user selecting action 2400 to decrease the width 2401 of the instrument positioning map. As can be seen in FIGS. 21-24, the AR overlay may be further resized and manipulated to better suit the user's body size.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

For example, the foregoing description provides the generation of complex instrument positioning maps by a server and shown to a user using graphical mapping locations in an AR view. However, it should be understood that various embodiments of the systems and methods discussed herein may be performed locally, for example, at a clinician's computing device, and/or the like.

The invention claimed is:

1. A system comprising one or more processors and memory, wherein the memory stores instructions that, when executed by the one or more processors, configure the system to:
   receive image data generated by an image tracking device, wherein the image data comprises (a) one or more images of a body of a patient captured in real-time and (b) a known visual landmark (i) sized for the patient and (ii) positioned at a defined position on the body;
   receive user input generated by an input device, wherein (a) the input device enables interaction with the image data, and (b) the user input identifies one or more mapping locations for each of one or more instruments relative to the known visual landmark in the image data;
   generate an instrument positioning map for the patient by overlaying the one or more mapping locations onto the image data, wherein the instrument positioning map indicates the one or more mapping locations for each of the one or more instruments relative to the known visual landmark; and
   store the instrument positioning map for access by a user, wherein the instrument positioning map is configured to be identified based on a unique identifier (a) positioned on the known visual landmark and (b) associated with the instrument positioning map.

2. The system of claim 1, wherein the instructions, when executed by the one or more processors, further configure the system to:
   generate the unique identifier for identifying the instrument positioning map.

3. The system of claim 1, wherein the instructions, when executed by the one or more processors, further configure the system to:
   identify a measurement reference characteristic of the image data; and
   responsive to identifying the measurement reference characteristic, transform the instrument positioning map.

4. The system of claim 3, wherein the measurement reference characteristic comprises at least one of the patient's body chest (a) shape or (b) size.

5. The system of claim 1, wherein the instructions, when executed by the one or more processors, further configure the system to:
   receive a resize action responsive to user engagement of a resize action element; and
   transform the instrument positioning map.

6. The system of claim 1, wherein the instructions that, when executed by the one or more processors, further configure the system to:
   store a reference to the known visual landmark.

7. A method comprising:
   receiving, by one or more processors, image data generated by an image tracking device, wherein the image data comprises (a) one or more images of a body of a patient captured in real-time and (b) a known visual landmark (i) sized for the patient and (ii) positioned at a defined position on the body;
   receiving, by the one or more processors, user input generated by an input device, wherein (a) the input device enables interaction with the image data and (b) the user input identifies one or more mapping locations for each of one or more instruments relative to the known visual landmark in the image data;
   generating, by the one or more processors, an instrument positioning map for the patient by overlaying the one or more mapping locations onto the image data, wherein the instrument positioning map indicates the one or more mapping locations for each of the one or more instruments relative to the known visual landmark; and
   storing, by the one or more processors, the instrument positioning map for access by a user, wherein the instrument positioning map is configured to be identified based on a unique identifier (a) positioned on the known visual landmark and (b) associated with the instrument positioning map.

8. The method of claim 7, further comprising:
   generating, by the one or more processors, the unique identifier for identifying the instrument positioning map.

9. The method of claim 7, further comprising:
   identifying, by the one or more processors, a measurement reference characteristic of the image data; and
   responsive to identifying the measurement reference characteristic, transforming, by the one or more processors, the instrument positioning map.

10. The method of claim 9, wherein the measurement reference characteristic comprises at least one of the patient's body chest (a) shape or (b) size.

11. The method of claim 7, further comprising:
    receiving, by the one or more processors, a resize action responsive to user engagement of a resize action element; and
    transforming, by the one or more processors, the instrument positioning map.

12. The method of claim 7, further comprising:
    storing, by the one or more processors, a reference to the known visual landmark.

13. A computer program product comprising a non-transitory computer readable medium having computer program instructions stored therein, the computer program instructions when executed by one or more processors, cause the one or more processors to:
    receive image data generated by an image tracking device, wherein the image data comprises (a) one or more images of a body of a patient captured in real-time and (b) a known visual landmark (i) sized for the patient and (ii) positioned at a defined position on the body;
    receive user input generated by an input device, wherein (a) the input device enables interaction with the image data and (b) the user input identifies one or more mapping locations for each of one or more instruments relative to the known visual landmark in the image data;
    generate an instrument positioning map for the patient by overlaying the one or more mapping locations onto the image data, wherein the instrument positioning map indicates the one or more mapping locations for each of the one or more instruments relative to the known visual landmark; and store the instrument positioning map for access by a user, wherein the instrument positioning map is configured to be identified based on a unique identifier (a) positioned on the known visual landmark and (b) associated with the instrument positioning map.

14. The computer program product of claim 13, wherein the computer program instructions further cause the one or more processors to:

generate the unique identifier for identifying the instrument positioning map.

15. The computer program product of claim 13, wherein the computer program instructions further cause the one or more processors to:

identify a measurement reference characteristic of the image data; and responsive to identifying the measurement reference characteristic, transform the instrument positioning map.

16. The computer program product of claim 15, wherein the measurement reference characteristic comprises at least one of the patient's body chest (a) shape or (b) size.

17. The computer program product of claim 13, wherein the computer program instructions further cause the one or more processors to:

receive a resize action responsive to user engagement of a resize action element; and transform the instrument positioning map.

* * * * *

UNITED STATES PATENT AND TRADEMARK OFFICE
CERTIFICATE OF CORRECTION

PATENT NO. : 11,813,121 B2
APPLICATION NO. : 16/830089
DATED : November 14, 2023
INVENTOR(S) : Thomas A. Rydberg It is certified that error appears in the above-identified patent and that said Letters Patent is hereby corrected as shown below:

On the Title Page

In Column 2, under "Primary Examiner", Line 1, delete "Sin-Wai Wu" and insert -- Sing-Wai Wu --, therefor.

In the Drawings

In sheet 8 of 26, FIG. 7B, reference numeral 720, Line 2, delete "identifer" and insert -- identifier --, therefor.

Signed and Sealed this
Twenty-second Day of October, 2024

*Katherine Kelly Vidal*

Katherine Kelly Vidal
*Director of the United States Patent and Trademark Office*